United States Patent
Oldham et al.

(10) Patent No.: US 8,834,797 B2
(45) Date of Patent: Sep. 16, 2014

(54) SCANNING SYSTEM AND METHOD FOR IMAGING AND SEQUENCING

(75) Inventors: Mark F. Oldham, Los Gatos, CA (US); Eric S. Nordman, Palo Alto, CA (US); Hongye Sun, Belmont, CA (US); Steven J. Boege, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 292 days.

(21) Appl. No.: 12/384,516

(22) Filed: Apr. 6, 2009

(65) Prior Publication Data

US 2009/0250615 A1    Oct. 8, 2009

Related U.S. Application Data

(60) Provisional application No. 61/042,621, filed on Apr. 4, 2008.

(51) Int. Cl.
    *C12Q 1/68*    (2006.01)
    *G01N 33/52*    (2006.01)

(52) U.S. Cl.
    USPC .................................. 422/82.08; 435/287.2

(58) Field of Classification Search
    USPC ......... 422/50, 425, 68.1, 82.05, 82.07, 82.08, 422/501, 502, 503; 436/94, 164, 172; 435/287.1, 287.2, 287.9; 506/33, 34, 506/35, 37, 39; 356/444
    See application file for complete search history.

(56) References Cited

U.S. PATENT DOCUMENTS

| | | | |
|---|---|---|---|
| 5,302,509 A * | 4/1994 | Cheeseman ................. | 435/6.11 |
| 5,307,148 A | 4/1994 | Kambara et al. | |
| 5,547,839 A * | 8/1996 | Dower et al. ................ | 435/6.11 |
| 5,754,291 A | 5/1998 | Kain | |
| 5,990,479 A | 11/1999 | Weiss et al. | |
| 6,052,401 A | 4/2000 | Wieser et al. | |
| 6,126,899 A | 10/2000 | Woudenberg et al. | |
| 6,207,229 B1 | 3/2001 | Bawendi et al. | |
| 6,207,392 B1 | 3/2001 | Weiss et al. | |
| 6,251,303 B1 | 6/2001 | Bawendi et al. | |
| 6,256,148 B1 | 7/2001 | Gasworth | |
| 6,261,779 B1 | 7/2001 | Barbera-Guillem et al. | |
| 6,274,323 B1 | 8/2001 | Bruchez et al. | |

(Continued)

FOREIGN PATENT DOCUMENTS

| | | |
|---|---|---|
| JP | 2001108684 | 4/2001 |
| JP | 2002005834 | 1/2002 |

(Continued)

OTHER PUBLICATIONS

Weiss, Shimon. "Fluorescence spectroscopy of single biomolecules." Science (1999) 283 1676-1683.*

(Continued)

*Primary Examiner* — Christopher A Hixson

(57) ABSTRACT

A scanning detection system is provided in which emissions from locations in a flow cell are detected. In some embodiments, the system can include an excitation source, a photocleavage source, and modulating optics configured to cause an excitation beam generated by the excitation source to irradiate a first group of the fixed locations and to cause a photocleavage beam generated by the photocleavage source to irradiate a second group of the fixed locations, which is separate and apart from the first group of fixed locations. Methods of detecting sequencing reactions using such a system are also provided.

31 Claims, 6 Drawing Sheets

(56) References Cited

U.S. PATENT DOCUMENTS

| | | |
|---|---|---|
| 6,306,310 B1 | 10/2001 | Bergmann et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,468,808 B1 | 10/2002 | Nie et al. |
| 6,744,502 B2 | 6/2004 | Hoff et al. |
| 6,809,810 B2 | 10/2004 | Carrillo |
| 6,839,179 B2 | 1/2005 | Boege et al. |
| 6,856,390 B2 | 2/2005 | Nordman et al. |
| 6,888,628 B2 | 5/2005 | Carrillo |
| 6,917,726 B2 | 7/2005 | Levene et al. |
| 7,006,215 B2 | 2/2006 | Hoff et al. |
| 7,012,141 B2 | 3/2006 | Lee |
| 7,139,074 B2 | 11/2006 | Reel |
| 7,157,572 B2 | 1/2007 | Lee |
| 7,169,939 B2 | 1/2007 | Lee et al. |
| 7,177,023 B2 | 2/2007 | Reel et al. |
| 7,248,359 B2 | 7/2007 | Boege |
| 7,265,833 B2 | 9/2007 | Oldham et al. |
| 7,280,207 B2 | 10/2007 | Oldham et al. |
| 7,329,860 B2 | 2/2008 | Feng et al. |
| 7,387,891 B2 | 6/2008 | Boege et al. |
| 7,402,671 B2 | 7/2008 | Lee |
| 7,498,164 B2 | 3/2009 | Oldham et al. |
| 7,518,764 B2 | 4/2009 | Osborne et al. |
| 7,791,013 B2 | 9/2010 | Wang et al. |
| 7,813,013 B2 | 10/2010 | Kain |
| 7,830,575 B2 | 11/2010 | Moon et al. |
| 7,960,685 B2 | 6/2011 | Feng et al. |
| 2004/0038390 A1 | 2/2004 | Boege et al. |
| 2005/0030534 A1 | 2/2005 | Oldham et al. |
| 2005/0123947 A1 | 6/2005 | Quake et al. |
| 2005/0244863 A1 | 11/2005 | Mir |
| 2006/0121602 A1 | 6/2006 | Hoshizaki et al. |
| 2006/0221336 A1 | 10/2006 | Boege et al. |
| 2006/0252070 A1 | 11/2006 | Boege et al. |
| 2007/0031875 A1* | 2/2007 | Buzby .......................... 435/6 |
| 2007/0036511 A1 | 2/2007 | Lundquist et al. |
| 2007/0077564 A1 | 4/2007 | Roitman et al. |
| 2007/0188750 A1 | 8/2007 | Lundquist et al. |
| 2007/0196834 A1 | 8/2007 | Cerrina et al. |
| 2007/0238679 A1 | 10/2007 | Rank et al. |
| 2007/0295917 A1 | 12/2007 | King |
| 2008/0003571 A1 | 1/2008 | McKernan et al. |
| 2008/0030628 A1 | 2/2008 | Lundquist et al. |
| 2008/0032301 A1 | 2/2008 | Rank et al. |
| 2008/0066549 A1 | 3/2008 | Oldham et al. |
| 2008/0105831 A1 | 5/2008 | Reel et al. |
| 2008/0153100 A1 | 6/2008 | Rank et al. |
| 2008/0176769 A1 | 7/2008 | Rank et al. |
| 2008/0220537 A1 | 9/2008 | Foquet |
| 2008/0226307 A1 | 9/2008 | Lundquist et al. |
| 2008/0241892 A1 | 10/2008 | Roitman et al. |
| 2009/0009767 A1 | 1/2009 | Boege et al. |
| 2009/0015912 A1 | 1/2009 | Ferenczi |
| 2009/0272914 A1 | 11/2009 | Feng et al. |

FOREIGN PATENT DOCUMENTS

| | | |
|---|---|---|
| WO | WO 96/27025 | 9/1996 |
| WO | WO-03/014400 | 2/2003 |
| WO | WO 2006/135782 A2 | 12/2006 |
| WO | WO-2007/049844 | 5/2007 |
| WO | WO-2009/123767 | 10/2009 |

OTHER PUBLICATIONS

Bentley, David R. "Whole-genome re-sequencing." Current Opinion in Genetics and Development (2006) 16 545-552.*

Shu, Dan et al. "Counting of six pRNAs of phi29 DNA-packaging motor with customized single-molecule dual-view system." The EMBO Journal (2007) 26 527-537.*

Squire, A. et al. "Three dimensional image restoration in fluorescence lifetime imaging microscopy." Journal of Microscopy (1999) 193 36-49.*

Semin, David J. et al. "Near-field optical microscopy nanoarray." Proc. SPIE (1997) 3009 109-118.*

Notification of Transmittal dated Jun. 5, 2009, from PCT Application No. PCT/US09/02150.

International Search Report dated Jun. 5, 2009, from PCT Application No. PCT/US09/02150.

Written Opinion of International Searching Authority dated Jun. 5, 2009, from PCT Application No. PCT/US09/02150.

Notification Concerning Transmittal of International Preliminary Report on Patentability mailed Oct. 14, 2010, in PCT/US/2009/002150.

International Preliminary Report on Patentability issued Oct. 5, 2010, in PCT/US/2009/002150.

Written Opinion of the International Searching Authority (transmitted with Notification mailed Oct. 14, 2010), in PCT/US/2009/002150.

200980120289.8, "Chinese First Office Action", *English Translation*, Dec. 5, 2012, 12 pages.

EP09728807.0 Extended Search Report, pp. 1-16, Jul. 11, 2011.

Jacak, J et al., Ultra-sensitive DNA detection on microarrays, *Proc. of SPIE*, vol. 5699, 2005, pp. 442-449.

Xu, G et al., Novel Design for Suspension Array Detection System, *Proc. of SPIE*, vol. 5630, 2005, pp. 417-421.

* cited by examiner

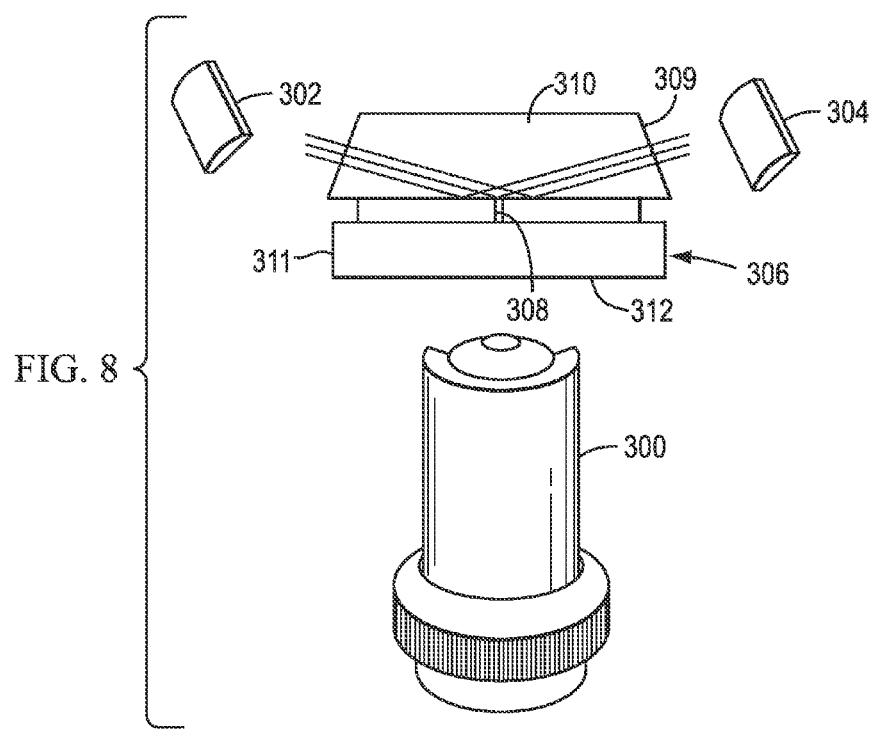

SCANNING SYSTEM AND METHOD FOR IMAGING AND SEQUENCING

CROSS-REFERENCE TO RELATED APPLICATIONS

This application claims benefit under 35 U.S.C. Section 119(e) from earlier U.S. Provisional Patent Application No. 61/042,621, filed Apr. 4, 2008, which is incorporated herein in its entirety by reference.

FIELD

The present teachings relate to scanning systems for image detection.

BACKGROUND

Various sequencing instrumentation, such as the SOLiD® system from Life Technologies Corporation, can use a tiling approach to create and/or generate imaging data. In such an approach, a stage capable of being positioned in X and Y dimensions may be used to move a portion of a slide or substrate, containing sequencing beads or other materials, into view of a camera or other imaging apparatus. Once positioned that stage can be stopped and allowed to settle prior to commencement of integration and/or imaging. This process can be repeated over a number of different iterations or cycles. It has been observed for various sequencing instrumentation, approximately the same amount of time is used to move the stage as to acquire sequencing data. Such systems may further take multiple scans, for example, one for each nucleotide, dye, or color (for a total of four or more scans). This type of system can be time consuming and costly. A need exists to reduce acquisition time, and reduce costs, while at the same time generating accurate sequence information.

Moreover, the benefits of raising excitation power are limited if the majority of time is not spent with the camera collecting emission photons, but is instead spent moving from one position to another. A need to address this limitation also exists.

SUMMARY

According to various embodiments of the present teachings, a system is provided for detecting emissions from a plurality of locations on a substrate. The system can comprise one or more irradiation sources configured to irradiate the substrate A first reaction, such as a fluorescence emission, can be made to occur at the first group of locations on the substrate. In some embodiments, a second, different reaction, can be made to occur at a second group of locations on the substrate. A scanning detector, for example, a detector array, can be included that is positioned with respect to the one or more irradiation sources so as to collect emission from the first group of locations and/or collect emission from the second group of locations.

Improvements to imaging approaches can be achieved by implementing multiple cameras or imaging devices for acquiring data simultaneously. Such systems can share a single excitation source for multiple cameras (for example, two or four cameras). As a result, the throughput of the system can be improved by making modifications to the imaging system. Such modifications may desirably be made while substantially leaving the rest of the system unchanged. Additionally, if the excitation power of the imaging system is increased, the integration time can be reduced, and the system speed can be correspondingly increased.

According to various embodiments of the present teachings, an imaging method is provided that can comprise imaging a ligation reaction. The method can further comprise the step of photocleaving protective groups from one or more of a plurality of polynucleotides after one or more scanning steps. A flow cell can comprise a plurality of beads therein, and a plurality of polynucleotides can be immobilized on the plurality of beads. A plurality of locations to be imaged can be locations occupied by the plurality of beads.

BRIEF DESCRIPTION OF DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings:

It is to be understood that both the foregoing general description and the following detailed description are exemplary and explanatory only and are intended to provide a further explanation of the various embodiments of the present teachings.

FIGS. 6-8 depict two consecutive positions as an objective with respect to an etched groove in a substrate, according various embodiments of the present teachings.

FIG. 9 illustrates a graph of probability versus time for a single labeled nucleotide incorporation event and a photocleavage operation, over the course of 3 seconds.

FIG. 10 is a further illustration of the graph of FIG. 9, over the course of 0.10 seconds.

FIG. 11 shows an exemplary set of prisms that can be used as mirrors for one or more irradiation beams and/or one or more emission beams during a scanning operation according to various embodiments.

FIG. 12A is a graph of excitation efficiency versus wavelength for four exemplary markers that can be used together, for example, as a set, according to various embodiments of the present teachings.

FIG. 12B is a graph of fluorescence intensity versus wavelength for the exemplary markers of FIG. 12A.

FIG. 13A is a graph of relative irradiation intensity versus wavelength for a pair of irradiation sources used according to various embodiments, wherein the irradiation beams generated by the two sources are of two different wavelengths (colors) and can be used to irradiate different or the same fixed locations on a substrate, simultaneously.

FIG. 13B is a graph showing percent transmission versus wavelength for a conditioning filter used to condition the beams represented in FIG. 13A.

FIG. 13C is a graph showing percent transmission versus wavelength for a bandpass filter used to filter light signals produced by markers excited by the light from the irradiation beams represented in FIG. 13A.

FIG. 13D is a graph showing relative emission intensity versus wavelength for the light filtered through the bandpass filter having the properties depicted in FIG. 13C.

FIG. 14 is an image of a substrate comprising a plurality of locations arranged in an orderly array, which substrate has been scanned according to various embodiments of the present teachings, wherein the image represents a square portion of the substrate.

FIG. 15 is an image of a substrate comprising a plurality of locations arranged in an non-orderly array, which substrate has been scanned according to various embodiments of the present teachings, wherein the image represents a square portion of the substrate.

FIG. 16 is a broken view of a substrate comprising a plurality of locations arranged in an orderly array, wherein the substrate is to be imaged according to various embodiments of the present teachings, and wherein the laser excitation beam used to excite markers at the locations is in the form of a line that has a width that is only about half of the width of each location along the line.

FIG. 17 is a top view of a linear image array aligned above the line of locations shown in FIG. 16, which has been irradiated with the excitation beam shown in FIG. 16, wherein wide pixels of the image array are shown centered with respect to the line of locations.

FIG. 18 is a broken view of a substrate comprising a plurality of locations arranged in an orderly array, wherein the substrate is to be imaged according to various embodiments of the present teachings, and wherein the laser excitation beam used to excite markers at the locations is in the form of a line that has a width that exceeds the width of each location along the line.

FIG. 19 is a top view of a linear image array aligned above the line of locations shown in FIG. 18, which line of locations has been irradiated with the excitation beam shown in FIG. 18, wherein pixels of the image array are shown centered with respect to the line of locations, plural pixels are shown above each location in the line, each pixel of the image array has a width that is less than the width of the respective location being imaged.

FIG. 20 is a broken view of a substrate comprising a plurality of locations arranged in an orderly array, wherein the substrate is to be imaged according to various embodiments of the present teachings, and wherein the laser excitation beam used to excite markers at the locations has been shaped into the form of an area beam having a width equal to the width of five lines of locations such that a first area of locations can simultaneously be irradiated with an excitation beam.

FIG. 21 is a top view of a two-dimensional image array aligned above the five-line area of locations shown in FIG. 20, which area of locations has been irradiated with the area excitation beam shown in FIG. 20, wherein pixels of the two-dimensional image array are shown above the area of locations, plural pixels are shown above each location in the area, each pixel of the image array has a width that is less than the width of the respective location being imaged, and the two-dimensional image array can be operated in a time-delay integration mode.

DESCRIPTION

Figure 1:
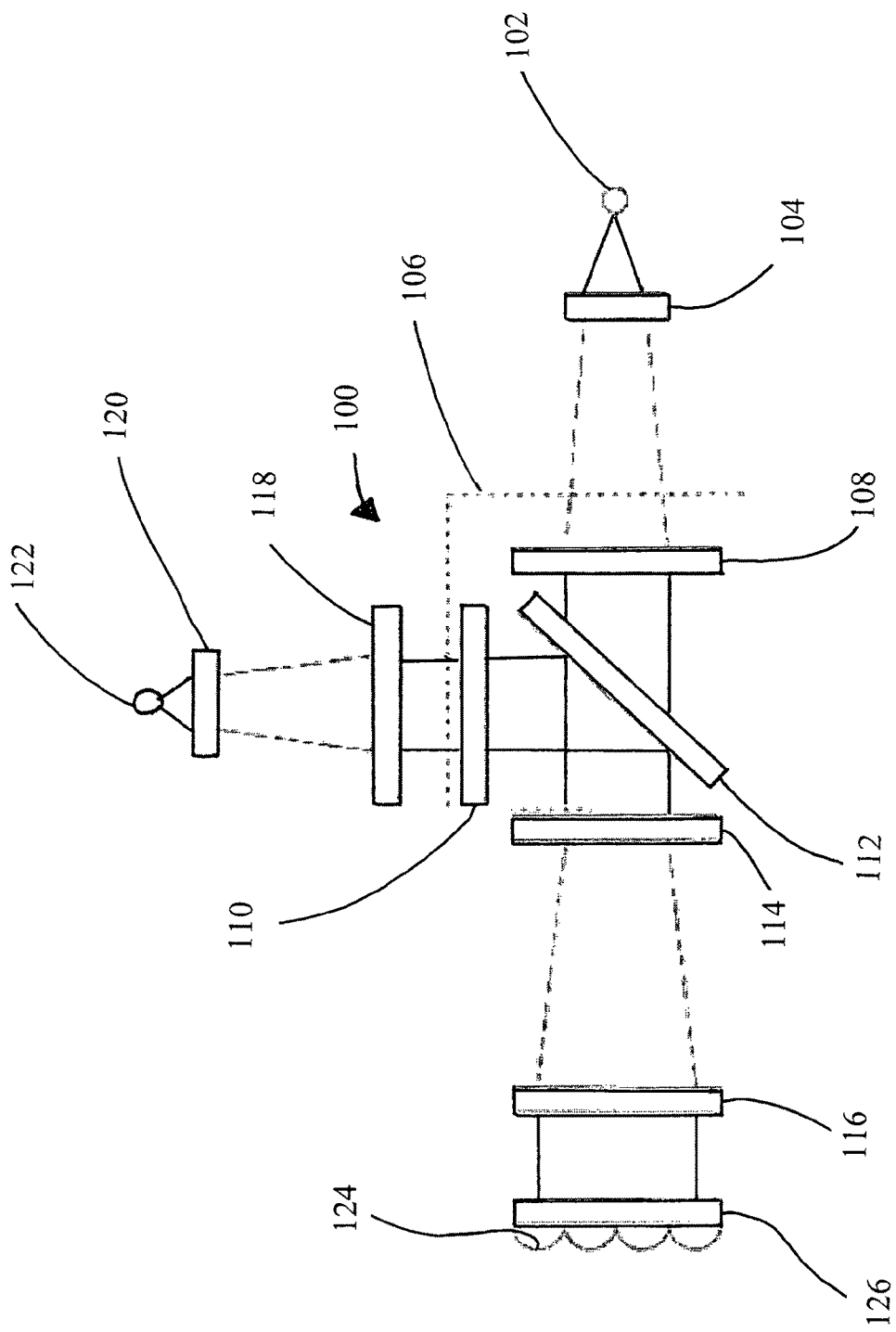
FIG. 1 illustrates a representative fluorometry scanning system according to various embodiments of the present teachings.

According to various embodiments of the present teachings, a system is provided for detecting emissions from a plurality of locations on a substrate, for example, fixed locations corresponding to locations of immobilized polynucleotides on a substrate. The system comprises a first irradiation source configured to irradiate the substrate and disposed for irradiating a first group of the locations, and a second irradiation source configured to irradiate a second group of the locations, wherein the second irradiation source is fixed with respect to the first irradiation source such that the second group of locations is spaced from and excludes the first group of locations on the substrate. As such, a first reaction, such as a fluorescence emission, can be made to occur at the first group of locations while a second, different reaction, for example, a photocleavage reaction, can be made to occur at the second group of locations. A scanning detector, for example, a detector array, can be included that is positioned with respect to the first irradiation source and the second irradiation source so as to collect emission from the first group of locations without collecting emission from the second group of locations. A translation stage can also be provided and configured to move the first irradiation source, the second irradiation source, and the scanning detector, with respect to each other.

In some embodiments, each location can correspond to the location of a polynucleotide, and at least some of the polynucleotides can be labeled with respective markers that fluoresce when exposed to excitation light. The system can comprise a substrate, wherein the substrate is positioned with respect to the first irradiation source so as to be irradiated by the first irradiation source. The substrate can comprise a flow cell and a plurality of labeled polynucleotides disposed in the flow cell. The flow cell can comprise a plurality of channels separated from one another.

The first irradiation source can comprise at least one laser source and a holographic beam shaper. The scanning detector can comprise a two-dimensional charge-coupled device. In some embodiments, the system can comprise modulating optics. The modulating optics can be disposed between the first irradiation source and the scanning detector. The scanning detector can comprise a point detector, a line detector, or an image detector.

In some embodiments, a system for detecting fluorescently labeled polynucleotides is provided, and comprises a substrate comprising a first end, a second end, one or more channels formed therein, and a plurality of labeled polynucleotide beads immobilized in the one or more channels, each of the labeled polynucleotide beads having a diameter and being labeled with a respective marker that is responsive to radiation and that emits emission light indicative of the presence of at least one nucleotide. The system can comprise at least one irradiation source for emitting radiation and disposed for irradiating the plurality of labeled polynucleotide beads to thereby excite the markers responsive to the radiation and to cause the markers to emit emission light. Modulating optics can be provided that comprise at least one of a cylindrical lens, a holographic beam shaper, and a set of prisms including at least one trombone prism. The modulating optics can be configured to shape radiation emitted from the at least one irradiation source onto a portion of the labeled polynucleotide beads such that the emitted radiation irradiates an area having a dimension that is the same as the diameter of the labeled polynucleotide beads, or smaller. The system can comprise a scanning detector array positioned with respect to the plurality of labeled polynucleotide beads, and configured to collect the emission light produced by the markers and to produce charges corresponding to the emission light. The detector array can have an output and a time-delay integration (TDI) system can be provided that accumulates charges corresponding to the emission light, within the detector array, and reads accumulated charges at the output of the scanning detector array.

In some embodiments, the system can comprise second modulating optics disposed between the at least one irradiation source and the scanning detector array. The second modulating optics can comprise a cylindrical lens. The TDI system can be configured to accumulate charge by moving, relative to one another, the at least one irradiation source and the plurality of labeled polynucleotide beads, without moving the at least one irradiation source and the scanning detector array relative to one another. In some embodiments, the TDI system can accumulate charge by moving relative to one another, the scanning detector array and the modulating optics.

The one or more locations can comprise over 500 locations, for example, over 1000 locations, over 10,000 locations, over 100,000 locations, over 1,000,000 locations, over 10,000,000 locations, or over 1,000,000,000 locations. The scanning detector array can be configured to collect emission light produced by markers in at one or more channels sequentially, for example, from 2 to 10 channels sequentially, about eight channels sequentially, at least 100 channels, sequentially, or the like. Each of the one or more channels can begin at the first end of the substrate and run continuously to the second end of the substrate.

According to various embodiments, a method for detecting a sequence of nucleotides of a polynucleotide is provided. The method can comprise generating a first beam of radiation with an excitation source, directing the first beam at a flow cell comprising a plurality of locations and a plurality of polynucleotides immobilized at the plurality of locations, then causing a first reaction in the flow cell, the first reaction involving at least some of the plurality of polynucleotides, and then scanning the flow cell with a scanning detector array, to detect radiation emitted from the plurality of fixed locations. In some embodiments, a scanning operation can occur before the first reaction. The method can further comprise irradiating the flow cell with a second beam of radiation generated by the same or a different excitation source, subsequent to the first reaction, for example, by radiation of a different wavelength. The flow cell can be scanned with the scanning detector array before and after the first reaction, to detect radiation emitted from the plurality of locations. A second reaction can then be caused in the flow cell, involving at least some of the polynucleotides. Then the flow cell can be irradiated with a third beam of radiation generated by the same or a different excitation source, subsequent to the second reaction. After again scanning the flow cell with the scanning detector array subsequent to the second reaction, to detect radiation emitted from the plurality of fixed locations, information ascertained from the scanning steps can be used to determine a sequence of nucleotides of one or more of the plurality of nucleotides.

The method can comprise a ligation reaction, for example, a ligation reaction before each scanning step. The method can optionally comprise the step of photocleaving protective groups from one or more of the plurality of polynucleotides after one or more of the scanning steps. The flow cell can comprise a plurality of beads therein, the plurality of polynucleotides can be immobilized on the plurality of beads, and the plurality of locations can be locations occupied by the plurality of beads. In some embodiments, the plurality of polynucleotides can comprise a plurality of single molecule polynucleotides each immobilized at a respective one of the locations.

In some embodiments, the method can further comprise shaping the first beam, the second beam, and the third beam with modulating optics disposed between the excitation source and the flow cell. The modulating optics can comprise at least one of a cylindrical lens, a holographic beam shaper, and a set of prisms comprising a trombone prism. The flow cell can comprise a plurality of channels or grooves formed therein, for example, the plurality of grooves can comprise only a few grooves, as in one, two, three, or four, or as many as at least 10,000 grooves. The plurality of polynucleotides can be immobilized on a plurality of beads and the beads can be disposed in the plurality of grooves. In some embodiments, the flow cell can comprise from 10,000 to 1,000,000,000 grooves for containing individual strands of DNA. In some embodiments, the plurality of polynucleotides can comprise at least some polynucleotides bearing protective groups, and the method can further comprise photocleaving the protective groups with a photocleavage beam source that differs from the excitation source.

In some embodiments, the method can comprise using a time delay integration system, for example, to generate a signal indicative of the presence or absence of a nucleotide at one or more of the fixed locations.

According to various embodiments, the present teachings refer to a scanning system and method. The system can be configured to detect biopolymers, for example, a biopolymer comprising a detectable signal. According to various embodiments, an optical system 100, is provided as shown in FIG. 1, and comprises a light source 122, an optical device 106 (shown generally as the features surrounded by the dotted line), a substrate 126 to be scanned, a detector 102, an excitation filter 120, and a second optical element 114. Light source 122, substrate 126, and detector 102 can be any of those as described herein. According to various embodiments, optical device 106 can comprise an optical device having structures similar to those described herein, such as an excitation filter 116, a beamsplitter 112, and an emission filter 108. Optical system 100 can also comprise a first optical element 116 and a second optical element 118 that may or may not be included in optical device 106.

According to various embodiments, first optical element 116 can comprise a mask, such as a mask, that includes a plurality of apertures. Each aperture can be adjusted to reduce non-uniformities in light emitted from the immobilized polynucleotides on substrate 126, which can include channels 124. For example, the arrangement of an aperture, such as the size and/or shape of the apertures, can be adjusted. In general, the apertures can be adjusted so light from locations having a similar volume and a similar concentration of sample, and that use a similar die will pass through the mask having a similar light signal, such as a similar relative response. As such, the signal reaching detector 102 will be an accurate representation of the reaction.

For example, although a first location and a second location of a substrate may contain similar volumes and concentrations of polynucleotides, and may also use similar dyes, the light from each of the first and second locations reaching the detector may not be similar. In various embodiments, a first aperture and a second aperture of the mask can be positioned next to the first channel and the second channel, respectively, of substrate 126. The arrangement of the first and second apertures can be adjusted so that non-uniformities in the light from the first and second locations that reach the detector can be reduced.

According to various embodiments, the first optical element 116 can comprise a plurality of lenses with each of the plurality of lenses having a unique numerical aperture (NA). The NA of the lenses, as well as the position of the lenses, can be adjusted to reduce the non-uniformities in light emitted from the markers in the channels of substrate 126. In some embodiments, the lenses can be molded to have the unique NA. In general, the NA can be adjusted so light from channels having a similar volume and a similar concentration of markers, and that use a similar die, will pass through the mask having a similar light signal. As such, the signal reaching detector 102 can be an accurate representation of the reaction.

According to various embodiments, the optical system can further comprise an additional optical element 114 that can comprise, for example, an additional filter such as a neutral density filter that can vary the transmission of the emitted light from locations on the substrate. For example, additional optical element 114 can vary the transmission based on the position of channels in substrate 126.

According to various embodiments, optical system 106 can further comprise a second optical element 114. Second optical element 114 can comprise a mask, a neutral density filter, or a lens having a predetermined NA. Second optical element 114 aids in reducing non-uniformities in the light from light source 106. Second optical element 114 can be positioned to reduce non-uniformities in the light from light source 122 before the light reaches the substrate 126.

According to various embodiments, the type of adjustment to optical elements 114 and 116 can be determined using any of a variety of techniques either separately or in combination. Exemplary techniques include sequential ray trace models, non-sequential ray trace models, radiometric formulae, empirical measurements of light reaching the sample space, and empirical measurements of light reaching the detector.

According to various embodiments, light is emitted from light source 122 and passes through excitation filter 124 and optionally through second optical element 114 before impinging on beamsplitter 112. A portion of the light impinging on beamsplitter 112 is directed locations on substrate 126 where it causes the samples to luminesce. The light emitted from the samples is passed through first optical element 116. The light is directed through filter 104 and detected by detector 102.

According to various embodiments, biopolymers can comprise an analyte, for example, one or more polynucleotides. The system can comprise one or more biopolymers that comprise an intrinsically detectable signal, and/or biopolymers that have been derivitized with a label or marker that confers a desired type of detectability. Various methods for labeling analytes with detectable moieties are well known in the art, such as excitable reporters, radioactive isotopes, fluorescent dyes, spin labels, chemiluminescent compounds and the like to stimulate detectable emission indicative of the nature of the analyte. When the analyte is a polynucleotide, labeling by hybridization with a labeled probe can also be used. The analyte can be labeled with a dye marker, a fluorescing dye, a free-floating dye, a reporter dye, a probe dye, an intercalating dye, a quantum dot, a molecular beacon, a linear probe, a quantum dot media, a quantum dot bead, a dye-labeled bead, a dye attached to an analyte associated with a bead, or a combination thereof. The marker can be responsive to radiation and can be configured to emit emission light indicative of the presence of at least one nucleotide.

Exemplary analytes can include nucleic acids, both single and double stranded, proteins, carbohydrates, viruses, cells, whole cells, single molecules, polymerases, organelles, organic polymers, other biological samples, particles, labeled media, labeled beads, and the like. The analytes can include biomolecules, for example, cells, proteins, DNA, RNA, polynucleotides, polypeptides, polysaccharides, and small molecule analytes. In some embodiments, the analyte can comprise a polymerase or other enzyme suitable for an extension reaction. According to various embodiments, the analyte can be a selected-sequence polynucleotide, and an analyte-specific reagent including a sequence-selective reagent for detecting the polynucleotide can be associated with the polynucleotide. Polynucleotide analytes can be detected by any suitable method, for example, polymerase chain reaction, ligase chain reaction, oligonucleotide ligation assay, hybridization assay, antibody assay, affinity assay, streptavidin/biotin assay, single base extension reaction, or a combination thereof.

An example of a marker compound can be a dye marker. Any suitable marker, such as, for example, a fluorophore, can be used. Fluorophores useful according to various embodiments can include those that can be coupled to organic molecules, particularly proteins and nucleic acids, and that can emit a detectable amount of radiation or light signal in response to excitation by an available excitation source. Suitable markers can encompass materials having fluorescent, phosphorescent, and/or other electromagnetic radiation emissions. Irradiation of the markers can cause them to emit light at varying frequencies depending on the type of marker used.

In some embodiments, a quantum dot can be incorporated into the system to facilitate detection of a polynucleotide or reaction product thereof. Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. In some embodiments, quantum dots can be used as a means to localize excitation for fluorophores utilizing FRET. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, colorimetric enzymes, or colloidal gold, can be improved with quantum dot nanocrystal-tagged conjugates. An exemplary quantum dot implementation is available from Quantum Dot Corporation of Haywood, Calif. under the trademark QDOT. More information about quantum dots and their applications can be found at, for example, www.qdots.com, and in U.S. Pat. Nos. 6,207,229, 6,251,303, 6,306,310, 6,319,426, 6,322,901, 6,326,144, 6,426,513, and 6,444,143 to Bawendi et al., U.S. Pat. Nos. 5,990,479, 6,207,392, and 6,423,551 to Weiss et al., U.S. Pat. No. 6,468,808 to Nie et al., and U.S. Pat. No. 6,274,323 to Bruchez et al., which describe a variety of biological applications, methods of quantum dot manufacturing, and apparatuses for quantum dot nanocrystals and conjugates, all of which are incorporated herein by reference, in their entireties.

According to various embodiments, the detection system and method of the present teachings can be used with biopolymers that have been labeled with energy transfer dyes. Energy transfer dyes can comprise a large Stokes' shift (i.e., the difference between the wavelength at which the dye has maximum absorbance and the wavelength at which the dye has maximum emission) so that the fluorescent emission is readily distinguished from the light source used to excite the dye. Examples of energy transfer dyes are described in U.S. Pat. Nos. 7,012,141 B2, 7,157,572 B2, and 7,402,671 B2 to Lee, and in U.S. Pat. No. 7,169,939 B2, to Lee et al., all of which are incorporated herein by reference, in their entireties. Energy transfer dyes like the ones that can be used with the present invention, can comprise fluorescein-cyanide conjugates, for example, BigDyes®, available from Applied Biosystems, LLC, Foster City, Calif. In some embodiments, a quantum dot can be used as the donor.

According to various embodiments, the system can comprise a substrate. The one or more biopolymers can be disposed on or in the substrate. The substrate can comprise one or more reaction regions. As referred to herein, a reaction region can comprise a channel, a flow cell, a groove, a trench, a well, an opening, a trough, or any combination thereof. The reaction region can be partially open to the surrounding environment or enclosed from the surrounding environment. In some embodiments, the biopolymers can be disposed on the surface of a reactant region. In some embodiments the biopolymers can be disposed in the reactant region. One example of the type of substrates that comprise one or more reactant regions can be found in International Publication No. WO 2006/135782 A2, to Nordman et al., which is incorporated herein by reference, in its entirety.

According to various embodiments, the one or more reaction regions can comprise a reaction surface disposed therein. The reaction surface can be, for example, the surface of a labeled bead. The bead can further be immobilized to the reaction region, or the bead can be adapted to move around within a reaction region. In some embodiments, the reaction region itself can comprise a reaction surface. The reaction region can comprise one or more labeled analytes immobilized on its surface, or immobilized within the reaction region. In some embodiments, the analytes can be immobilized in a non-orderly manner, or in an orderly manner. Examples of immobilization and mobilization of analytes on a substrate can be found in U.S. Patent Application Publication No. US 2008/0241892 A1, to Reel et al., U.S. Patent Application No. US 2008/0105831 A1, to Reel et al., U.S. Patent Application Publication No. US 2008/0220537 A1, to Foquet, U.S. Patent Application Publication No. US 2008/0176769 A1, to Rank et al., and International Publication No. WO 2006/135782 A2, to Nordman et al., all of which are incorporated herein by reference, in their entireties.

In some embodiments, the reaction region surface, for example a bead surface, can comprise attachment characteristics. The surface can comprise low-density reactive groups, for example, the low-density substrate described in U.S. Patent Application Publication No. US 2007/0077564 A1, to Roitman et al., which is incorporated herein by reference, in its entirety. The reaction region surface can comprise active regions thereon, for example, the enzyme attachment and exclusion surfaces described in U.S. Patent Application Publication Nos. US 2007/0238679 A1, US 2008/0032301 A1, US 2008/0153100 A1, US 20080176769 A1, to Rank et al., and US 2008/0003571 A1 to McKernan et al., all of which are incorporated herein by reference, in their entireties.

According to various embodiments, the system can comprise a stage. The stage can be configured to receive and hold one or more substrates. The stage can be configured to move in an X and Y axis of rotation, thereby causing the one or more substrates to move in an X and Y axis of rotation. The stage can be configured to move a portion of a substrate into view of a detector or other imaging apparatus. Once positioned the stage can be configured to stop, and the stage can settle prior to commencement of imaging. In some embodiments, the stage is in continuous motion, such that the stage does not stop until the entire substrate has been detected by the detector. In some embodiments, the stage can move the objective with respect to the detector and substrate, or the detector and objective can be moved with respect to the substrate.

According to various embodiments, the system can comprise one or more detectors. As referred to herein, a detector can comprise a detector array, an objective, an objective lens, a camera, a photodetector, a charge-coupled device (CCD), a complimentary metal-oxide-semiconductor (CMOS) device, a point scanner, a line scanner, an image scanner, another type of optical detector, or a combination thereof. The detector can also comprise a plurality of detectors, for example, two detectors, four detectors, or any other amount of detectors desired. In some embodiments, the detector can be configured to detect multiple optical signals from a single source, for example, the systems described in U.S. Patent Application Publication No. US 2007/0036511 A1, to Lundquist et al., which is incorporated herein by reference, in its entirety. In some embodiments, the detector can be configured to detect simultaneous real-time monitoring of optical signals from multiple sources, for example, the systems described in U.S. Patent Application Publication Nos. US 2007/0188750 A1, and US 2008/0030628 A1, to Lundquist et al., and in U.S. Pat. No. 6,856,390 B2 to Nordman et al., all of which are incorporated herein by reference, in their entireties.

According to various embodiments, the detector can comprise a time-delay integration (TDI) system. In the detector, photogenerated charge collected in the photoactive elements or pixels of the detector can be transferred toward a serial register one row at a time. The charge information in the serial row can be read by using a corresponding single on-chip amplifier or readout register of the detector. By way of example, for a 256×256 element CCD, each time a single imaging area (one row) is transferred to the serial register, n readouts (where n corresponds to the length of the area to be scanned) of the thus transferred area are performed, each readout corresponding to a different spectral element or pixel in the row. The above process continues until all 256 pixels in all 256 rows have been read.

Figure 2:
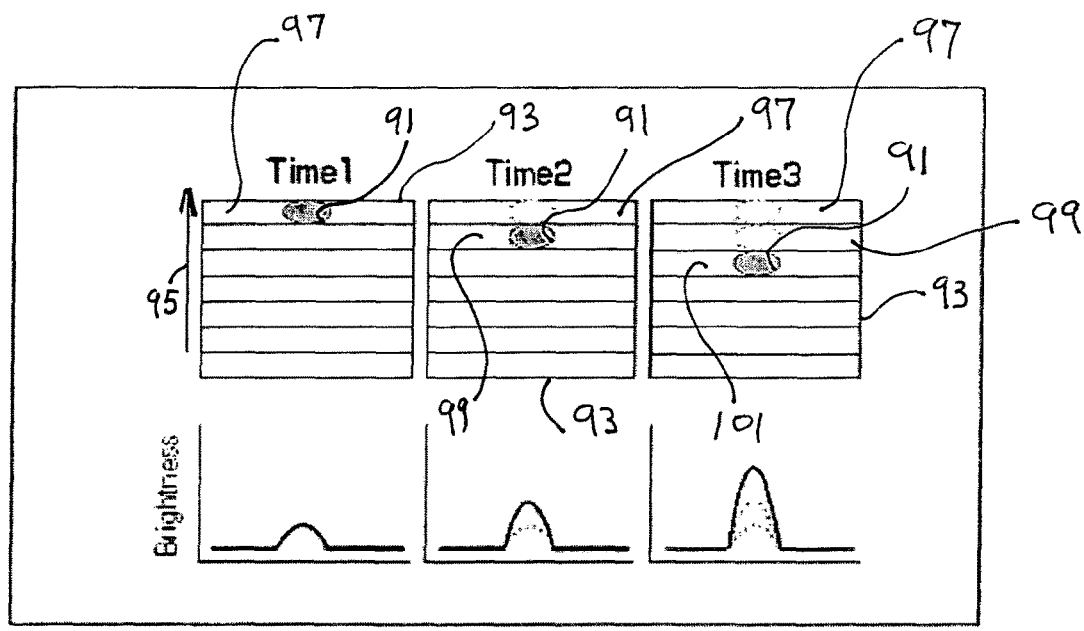
FIG. 2 depicts a system and method according to various embodiments using a time-delay integration made whereby a detector array is scanned across a fixed location and brightness measured sequentially by various pixels is compounded to enhance the detected signal.

FIG. 2 shows an exemplary time-delay integration process that can be embodied according to the present teachings. As shown in FIG. 2, a detector array 93 can be scanned in a direction depicted by directional arrow 95 across a fixed location 91 on a substrate. According to various embodiments, the fixed location can comprise the location at which a polynucleotide is immobilized and has been reacted to emit radiation. As shown in FIG. 2, emitted radiation from fixed location 91 is detected at Time1 by a first array pixel 97, and the radiation emitted has been measured with respect to brightness as shown in the graph underneath the configuration shown at Time1.

According to the method depicted in FIG. 2, scanning movement of detector array 93 in direction 95 results in the positioning of pixel 99 over fixed location 91 at Time2. Brightness measured at Time2 is then compounded to the brightness measured by pixel 97 at Time1 and the compounded brightness is shown in the graph below the configuration shown at Time2. According to the method depicted, the scanning operation then results in the configuration shown at Time3, whereby the detector array has been moved in direction 95 to the point where pixel 101 is located above the omission radiated from fixed location 91. Brightness measured by pixel 101 at Time3 is then compounded with the brightness measured by pixel 99 at Time2 and the brightness measured by pixel 97 at Time1 to form a compounded brightness graph shown below the configuration depicted in Time3.

This and similar time-delay integration methods can be used according to various embodiments of the present teachings.

Figure 3:
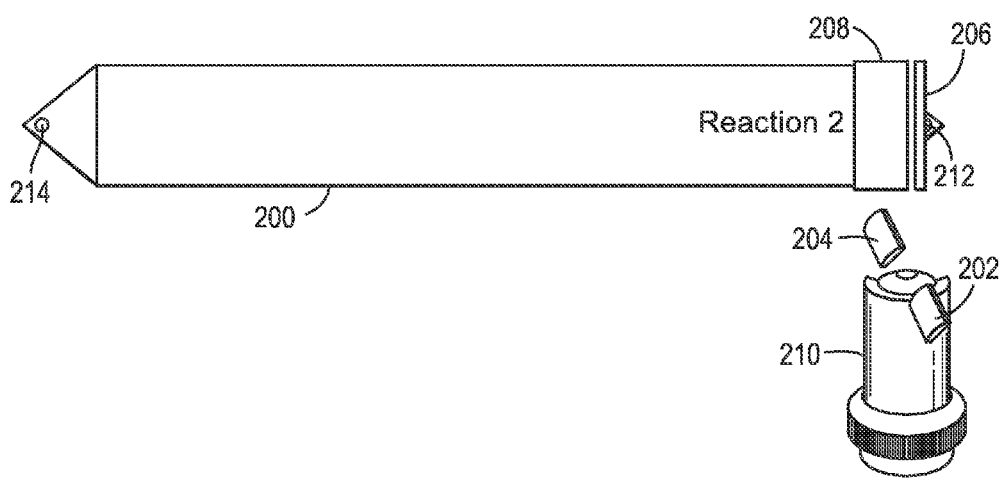
FIG. 3 depicts an embodiment of a time-delay integration single molecule sequencing scanning system that can be used according to various embodiments of the present teachings.
Figure 4:
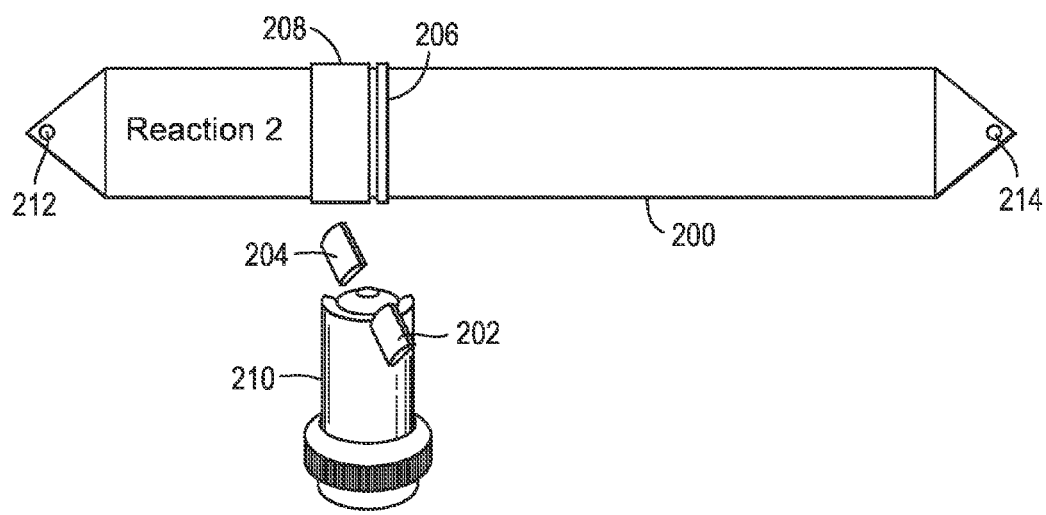
FIG. 4 depicts the same flow cell and a scanning system depicted in FIG. 3 above a first, early position during a scanning operation.
Figure 5:
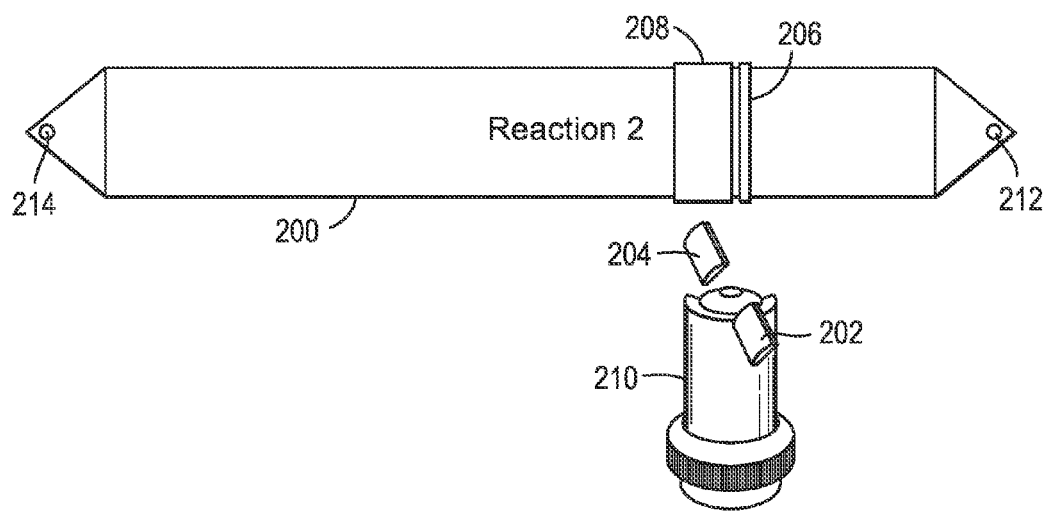
FIG. 5 depicts the same scanning system shown in FIGS. 3 and 4, but at a later position during a scanning operation relative to the position depicted in FIG. 4.

According to various embodiments, another scanning system according to various embodiments of the present teachings is depicted in FIGS. 3-5. It is to be understood that the features of the optical configuration shown in FIG. 1 and the time-delay integration system and method shown in FIG. 2 can be incorporated in whole, in part, or not at all, in connection with the system depicted in FIGS. 3-5. Although FIG. 3 labels the scanning system as a time-delay integration, single molecule sequencing (TDI SMS) scanning system, it is to be understood the system does not necessarily have to operate in a time-delay integration mode. Furthermore, it is to be understood that the system can be used in the detection of any emission in general from locations on a substrate, for example, to detect multiple copies of polynucleotides immobilized on a single bead, for example, where many such beads are immobilized on a substrate. By "immobilized," with reference to the beads, it is to be understood that the beads need not be physically or chemically bound to the substrate, but rather, can simply rest on the substrate but be restricted from movement with respect to the substrate during a scanning operation.

As shown in FIGS. 3-5, the system can be used to detect reactions on a substrate, for example, reactions in a flow cell 200 as depicted. Flow cell 200 can be provided with a first input port 212 and an output port 214, between which reagents, reactants, or other materials can be transported to effect various reactions in flow cell 200. Flow cell 200 can be, but is not necessarily, provided with a plurality of grooves or channels formed therein or thereon. In some embodiments, exemplary grooves or channels can comprise those described in U.S. Pat. No. 6,856,390 B2 to Nordman et al. The scanning system can comprise a detector having at least an objective lens 210 that can be configured to detect emission from a first area 206, on or adjacent, flow cell 200. The system can comprise two irradiation sources (not shown), the first of which can comprise an excitation source configured to generate an excitation beam and direct the excitation beam to modulating optics 202, depicted in FIGS. 3-5 as a cylindrical lens 202. Another irradiation source (not shown) can be configured to generate a photocleavage radiation beam toward and through second modulating optics 204, depicted as a cylindrical lens 204. According to various embodiments, modulating optics 202 are configured to direct the excitation beam at area 206 in a manner such that the excitation beam is shaped to fall incident on flow cell 200 in the form of area 206. Similarly, the photocleavage beam modulated by modulating optics 204 can be directed at, and shaped to fall incident on, area 208. As can be seen, objective 210 is configured to detect emission from area 206 without detecting emission from area 208. A scanning operation depicting use of such a system is shown in FIGS. 4 and 5.

As shown in FIG. 4, the system depicted in FIG. 3 is shown at a first position during an early portion of a scanning operation. During operation, the entire system, but not including flow cell 200, is moved in the direction from left to right such that, after a period of time, the system is moved to a later position depicted in FIG. 5. Such scanning, depicted in the sequential steps shown in FIGS. 4 and 5, shows that the system operates to irradiate area 206 over flow cell 200 with an excitation beam, and to detect radiation emitted from area 206 using objective 210. In the situation where objective 210 is part of a detection system comprising a detector array, for example, an array of pixels, it should be appreciated that the pixels can be individually dedicated to various locations in flow cell 200 that fall within area 206. It should also be appreciated that locations in flow cell 200 that are within area 208 can be subjected to a photocleavage beam separate and apart from the excitation beam that is directed to area 206. Thus, the system can provide excitation of locations in area 206 while simultaneously providing photocleaving reactions at locations in area 208.

As can be seen from the movement depicted from the position shown in FIG. 4 to the position shown in FIG. 5, shortly after an excitation and detection operation at locations in the flow cell within area 206, the same locations are then subjected to a photocleavage beam and a photocleavage operation. According to various methods, subsequent to a polynucleotide being subject to a photocleavage operation, an additional nucleotide can thereafter be incorporated onto the polynucleotide which had been subjected to the photocleavage operation.

Figure 6:
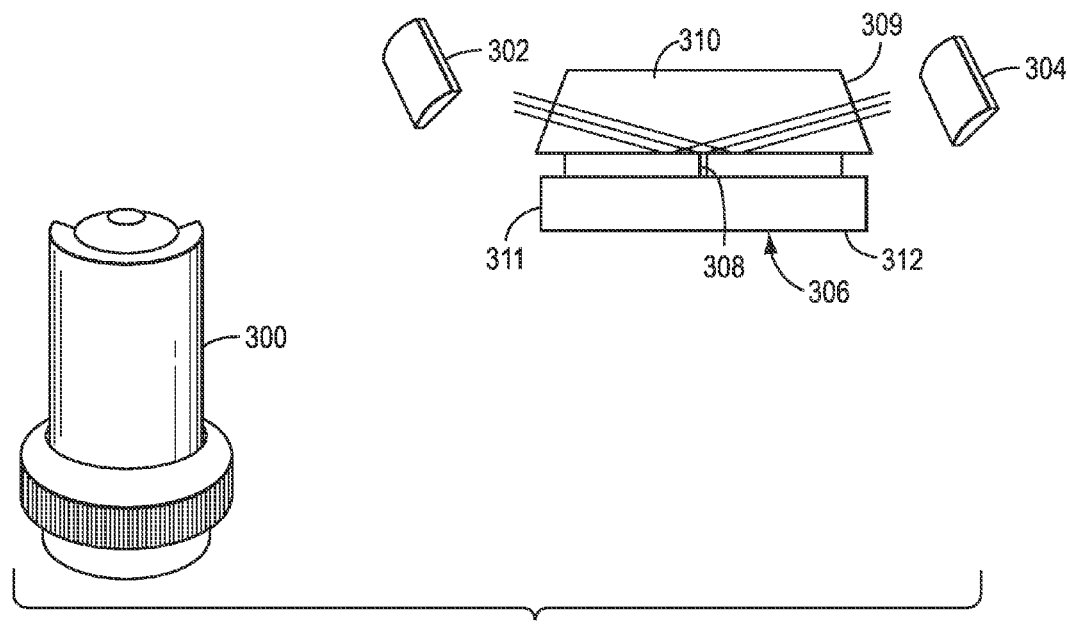
Figure 7:
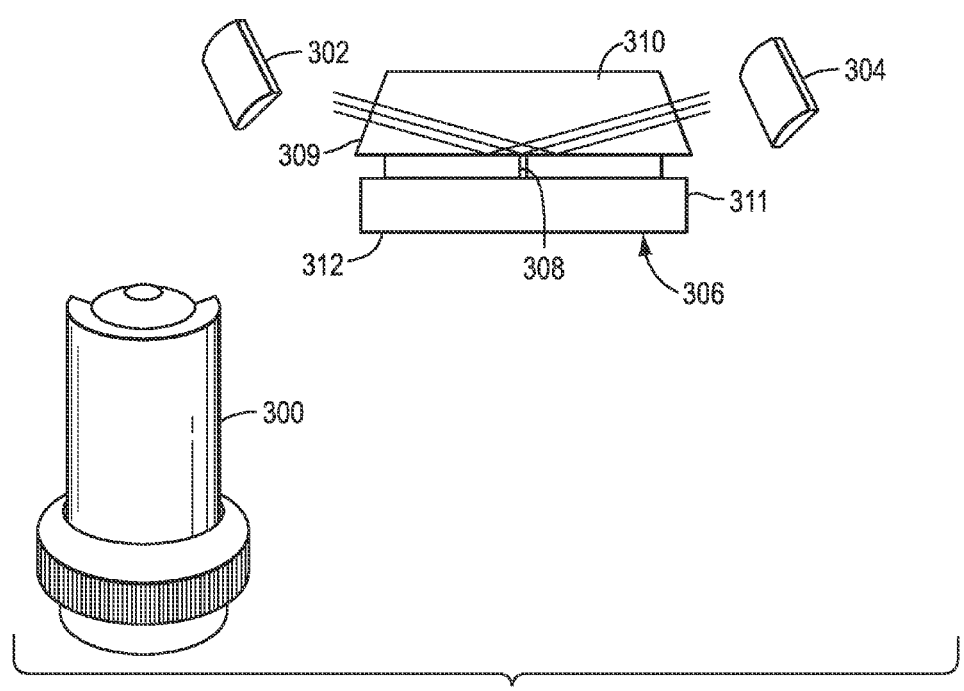

Another embodiment of a scanning detection system according to various embodiments of the present teachings is depicted in FIGS. 6-8. FIGS. 6-8 depict a sequence of movements of an objective 300 toward and into close proximity with a flow cell 306 comprising a channel 308. In the embodiments shown, excitation beams shaped by modulating optics 302 are directed to a first side 310 of flow cell 306. Also, a photocleavage beam shaped by modulating optics 304 is also directed to first side 310 of flow cell 306. As can be seen in FIG. 8, objective 300 detects emissions from locations within channel 308, from a bottom side 312 of flow cell 306, which is opposite top side 310 onto which the excitation beam and photocleavage beam are directed on their ways toward channel 308. In the exemplary embodiments shown, the reaction locations can be on the underside of the flow cell wall 309 bearing top surface 310. In such an embodiment, the objective has a working distance that includes detecting through bottom substrate 311 of flow cell 306 and through any reagent in channel 308.

In some embodiments, TDI can be achieved by moving, relatively to one another, the substrate and the detector. Under a normal read-out approach, the motion of the images on the detector produces a blur. In TDI, the shutter can be eliminated. In some embodiments, the shifting of rows of the detector can be synchronized to the movement of the substrate/stage. After this time period, the charge on the detector can be shifted one row closer to the serial register, such that the fluorescence from the analyte corresponds to the same charge information on the detector. Therefore, distinct from the physical rows of the detector, there exists in TDI according to various embodiments, sets of continuously moving rows of accumulating photogenerated charge. Exemplary TDI systems can be found in FIGS. 1, 10, and 11 of U.S. Pat. Nos. 7,280,207 B2, and 7,265,833 B2, to Oldham et al., both of which are incorporated herein by reference, in their entireties.

According to various embodiments, the system can comprise one or more filters. As referred to herein, a filter can comprise an emission filter, an excitation filter, a multi-notch filter, a Rugate filter, a dichroic filter, bandpass filters, or a combination thereof. In some embodiments, a filter can be a single bandpass filter or a multiple bandpass filter. As used herein, a bandpass filter and a passband filter can be used interchangeably. A multiple passband filter can be, for example, a multi-notch filter, a multi-Rugate filter, or simply a Rugate filter. A multiple passband filter can be used with an incoherent light source, for example, a halogen lamp, a white light source, and/or one or more Light Emitting Diode (LED), or Organic LEDs emitting light at different wavelengths. A multiple passband filter can be used with a multiple laser-based light source emitting light at different wavelengths.

Examples of manufacturing Rugate filters and Rugate beam splitters can be found in FIG. 1 of U.S. Pat. No. 7,498,164 B2, which is incorporated herein by reference, in its entirety.

According to various embodiments, the system can comprise various modulating optics. Modulating optics can include beam shapers, beam splitters, prisms, trombone prisms, sets of prisms, dichroic mirrors, lenses, cylindrical lenses, Fresnel lenses, focusing lenses, collimating lenses, or any combination thereof. The modulating optics can be disposed in the system, on path between the irradiation source and the substrate. The modulating optics can be disposed on path between the substrate and the detector. In some embodiments, the modulating optics can comprise one or more holographic elements, for example, a holographic beam shaper. The one or more holographic optical elements can be used to diffract light at various angles. The holographic beam shaper can create a "top hat" pattern, and can further distribute the light such that it compensates for other parts of the optical system, such as making the edges brighter to compensate for vignetting. Examples of holographic optical elements are described in U.S. Pat. Nos. 6,744,502 and 7,006,215, to Hoff et al., both of which are incorporated herein by reference, in their entireties. In some embodiments excitation enhancements can be used to enhance energy levels, for example, the plasmons described in U.S. Patent Application Publication No. 2008/0066549 A1, to Oldham et al., which is incorporated herein by reference, in its entirety. TDI detection can be performed by moving modulating optics relative to irradiation, by moving irradiation relative to the substrate, and/or by moving optics and the substrate.

In some embodiments, modulating optics can be configured to combine multi-spectral light from spatially separated sources. The use of various optical elements to combine two different light sources are exemplified in FIGS. 1A-7B, of U.S. Pat. No. 7,248,359, to Boege, which is incorporated herein by reference, in its entirety. In some embodiments, the system can be a system that is configured to operate in zero-mode waveguide (ZMW). A zero mode waveguide system is exemplified in FIG. 3 of U.S. Patent Application Publication No. US 2008/0226307 A1, to Lundquist et al., and FIGS. 1-2 of U.S. Pat. No. 6,917,726 B2 to Levene et al., both of which are incorporated herein by reference, in their entireties.

According to various embodiments, the substrate itself can be configured to direct excitation and emission light, for example, the detection cell described in U.S. Pat. Nos. 6,809,810 B2, and 6,888,628 B2 to Carrillo, both of which are incorporated herein by reference, in there entireties.

According to various embodiments, the system can comprise one or more irradiation sources. The source of irradiation can be any of a variety of light sources. The irradiation source can be, for example, an LED, an organic LED, a non-coherent light source as known to those skilled in the art, a solid state laser, a microwire laser, a white light source, or a combination thereof. As used herein, the terms "irradiation source," "light source," "excitation source," or the like can include single or multiple sources of irradiation. As used herein, "LED" can refer to an LED, an OLED, or multiplicities thereof. Further, according to various embodiments, the "LED" can include coherent irradiation sources, for example, a solid state laser source or a micro-wire laser source. Each irradiation source can be configured to irradiate the substrate. Each irradiation source can be configured to irradiate a fixed location or a group of fixed locations on the substrate.

In some embodiments, the system can comprise two or more irradiation sources. A first irradiation source can be configured to irradiate the substrate, and be disposed for irradiating a first group of fixed locations of a plurality of fixed locations. A second irradiation source can be configured to irradiate a second group of fixed locations of the plurality of fixed locations. The second irradiation source can be fixed with respect to the first irradiation source such that the second group of fixed locations is spaced away from and excludes the first group of fixed locations on the substrate. In some embodiments, the first group of fixed locations and the second group of fixed locations, partially overlap each other in X and/or Y direction. In some embodiments, the first group of fixed locations and the second group of fixed locations are the same. One or more detectors, for example, a scanning detector array, can be positioned with respect to the first irradiation source and the second irradiation source so as to collect emission from the first group of fixed locations without collecting emission from the second group of fixed locations. In some embodiments, scanning detector array can be positioned with respect to the first irradiation source and the second irradiation source so as to collect emission from both the first group of fixed locations and the second group of fixed locations.

The light emitted by markers immobilized on or in the substrate can be passed through a bandpass filter. The bandpass filter can allow, substantially exclusively, predetermined wavelengths of light from the substrate to pass through, wherein the predetermined wavelengths of light correspond to a portion of the wavelengths of the light signals emitted by an associated set of markers. The light that passes through the bandpass filter can be filtered light. The bandpass filter can substantially block the irradiation light from the irradiation sources if such light is reflected from the substrate. The portion of the wavelengths of the light signals that can pass through the bandpass filter can include all of the light signals, or a range of wavelengths about the peak intensity of light signals of each respective marker. For example, the range of wavelengths about the peak intensity of light signals can be between about 5% and about 20% of wavelengths on each side of the peak wavelength of a given marker, or it can include full width at half max. The collection of the predetermined wavelengths can be by dispersion, for example, or by use of additional bandpass filters, for example.

According to various embodiments, a conditioning filter can be used between the irradiation source (light source) and the substrate. The beam emitted by the light source is also known as an excitation beam if designed to excite a marker, and can be filtered by an excitation filter at an excitation wavelength range. Comparably, a conditioning filter can be used between a detection zone where a substrate is positioned, and a detector. The fluorescence or luminance emitted by the substrate upon excitation is also known as an emission beam that can be filtered by an emission filter at an emission wavelength range.

According to various embodiments, a light source can be used to provide excitation beams to irradiate a substrate having one or more markers immobilized thereon or therein. In some embodiments, two or more excitation beams having the same or different wavelength emissions can be used such that each excitation beam excites a different respective dye immobilized on the substrate. The excitation beam can be aimed from the light source directly at the substrate, through a wall of the substrate, or can be conveyed by various optical systems to the substrate, as described herein.

According to various embodiments, one or more filters, for example, a bandpass filter, can be used with a light source to control the wavelength of an irradiation beam. One or more filters can be used to control the wavelength of an emission beam emitted from an excited or other luminescent marker. One or more irradiation filters can be associated with a light source to form the irradiation beam. One or more filters can be located between the one or more light sources and a substrate. One or more emission filters can be associated with an emission beam from an excited dye. One or more filters can be located between the substrate and one or more emission beam detectors.

According to various embodiments, a filter can be used that is a single bandpass filter or a multiple bandpass filter. As used herein, a bandpass filter and a passband filter are used interchangeably. A multiple passband filter can be, for example, a multiple-notch filter or a multi-Rugate filter. A multiple passband filter can be used with an incoherent light source, for example, a halogen lamp, a white light source, and/or one or more LEDs or OLEDs emitting light at different wavelengths. A multiple passband filter can be used with a multiple laser-based light source emitting light at different wavelengths. Examples of manufacturing and use of Rugate filters and Rugate beam splitters can be found in, for example, U.S. Pat. No. 6,256,148 to Gasworth which is incorporated herein by reference, in its entirety.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A beam splitter can be disposed at a low angle along a light or beam path to sharpen edges of the filtered light and can ease fabrication. A beam splitter can be disposed at a 45° of incidence along a light beam path. A low angle can include an angle of incidence less than 45° less than 30° or less than 15°. A multiple passband filter can be formed by coating different light interference materials over respective areas of a substrate used in a multiple passband filter manufacture.

A Rugate filter is an example of an interference coating based on the refractive index that varies continuously in a direction, for example, perpendicular or 45° to the film plane. When the refractive index varies periodically within two extreme values, a minus filter with high transmittance on either side of the rejection band can be made. Periodic Rugate filters can be manufactured. Rugate notch filters can use refractory metal oxides to achieve coatings with exceptional thermal and environmental stability. These filters can be used in place of other types of notch filters, particularly where durability and reliability are desired. Rugate notch filters are available from Barr Associates (Westford, Mass.). The Rugate notch filter can be used as edge filters and beam splitters. Filter sizes or shapes are not limitations for the Rugate notch filter. The Rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, and www.barrassociates.com/opticalfilters.php. Multiple-notch filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally at different fixed locations are irradiated with excitation beams. This can lead to less spectral crosstalk. The dye matrix, condition number, and/or deconvoluting in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

According to various embodiments, the detector can comprise a detection assembly. An exemplary detection assembly can be used for fluorescence detection of target polynucleotides in a sample using a device in accordance with the invention. The detection assembly comprises a translation stage for positioning a test device. The test device can comprise an array of addressable detection chambers containing fluorescent detection reagents. The detector in the assembly can comprise a tungsten bulb (or quartz halogen bulb, 75 W) illumination source, a CCD camera, and appropriate focusing/collection optics. The illumination source can be positioned so as to illuminate the device diagonally from above (e.g., at an inclination angle of 45 degrees with respect to the illuminated surface). The optics can comprise two lenses separated by an emission filter. The first lens collimates the incoming image for the emission filter, and the second lens which re-images the filtered beam onto the CCD. The test device is placed at the focal point of the first lens.

In some embodiments, the CCD can be thermoelectrically cooled, instrumentation-grade front-illuminated CCD (Princeton Instruments TEA/CCD-512TK/1). The detection plate of the CCD can comprise a 512×512 array of 27 .mu.m square pixels which can cover the entire overhead cross-section of the test device. The camera head can be controlled by a controller (Princeton Instruments ST-135) which can communicate with a computer (Quadra 650, Apple Computers) for collecting and processing the signal data. The detection system can be capable of on-chip binning of the pixels. For detection chambers having an overhead cross-section of 1 mm.times.1 mm, bins having a size of 2×2 pixels are suitable. More generally, the bin size can be selected on the basis of the total processing time that will be required, the sizes and number of detection chambers, sensitivity, and signal noise.

According to various embodiments, the detection assembly can comprise a computer. The computer in the assembly can comprise signal-processing software for selecting an appropriate sub-region in each detection chamber from which the signal is measured. Such sub-regions can be selected for uniformity of incoming light, to ensure that edge regions are excluded. The signal image of the device can be recorded and stored at selected intervals, according to the requirements of the assay. Preferably, the signal for each detection chamber is recorded as an average signal per bin for the selected sub-region in each chamber, since the size of the selected sub-region in each chamber will usually differ from chamber to chamber. Examples of an addressable array are described in Woudenberg et al., U.S. Pat. No. 6,126,899, which is incorporated herein by reference, in its entirety.

Exemplary systems where the detection system and method of the present teachings can be incorporated, include, but are not limited to the following, a single molecule sequencing detection system as exemplified in FIGS. 1A, 1B, 3A, and 3B, of U.S. Patent Application Publication No. US 2008/0105831 A1, to Reel et al., a single excitation wavelength detection system as exemplified in FIG. 1 of U.S. Patent Application Publication No. US 2007/0295917 A1, to Howard, an optical system and method for optically analyzing light from a sample as exemplified in FIGS. 14 and 28 of U.S. Pat. No. 7,139,074 B2, to Reel, a fluorescent detection system as exemplified in FIGS. 9-11B and 13, of U.S. Pat. No. 7,177,023 B2, to Reel et al., an electrophoretic system with multi-notch filter and laser excitation source as exemplified in FIG. 1 of U.S. Pat. No. 7,265,833 B2, to Oldham et al., and a total internal reflectance fluorescence microscope or detection system as exemplified n FIG. 2 of U.S. Patent Application NO. US 2009/0015912 A1, to Ferenczi, all of which are incorporated herein by reference, in their entireties. The exemplary systems are merely examples of possible system configurations, and are not meant to limit the teachings of the present invention.

According to various embodiments, the system can comprise a line scanner approach to imaging. A system configured to implement a line scanner approach to imaging, can comprise a detector that is a single pixel in width in the scan direction. This approach eliminates most of the time spent moving from one position to another, allowing most of the time to be spent collecting emission photons. For single molecule systems where the turnover rate of the fluorophores is generally slow this can create issues with obtaining a sufficient signal to noise ratio at the scan speed desired to more fully utilize the camera. For a bead based sequencing system, an optical configuration may be conceived to effectuate an efficient line scan system, for example, the system exemplified in FIG. 1 of U.S. Pat. No. 7,265,833 B2, to Oldham et al., which patent is hereby incorporated by reference, in its entirety.

In some embodiments, a point scanner is used and can be configured in many ways, for example, the detector for a point scanner can comprise a single detector used for a single channel of detection. A beam-splitter or a set of beam-splitters can be used in some embodiments, permitting two or more channels of detection simultaneously. The excitation beam can similarly have a single bandpass, or can have multiple bandpasses used simultaneously or serially.

For next generation sequencing applications, where beads are used that are typically on the order of one micron in diameter, it is reasonable to achieve an optical resolution of only 500 nm. If a pixel width in the scan axis corresponding to one micron is used, the optical resolution is convolved with the pixel width, resulting in an effective width of 1.5 microns. Thus if one micron beads were too close to each other, they might not be able to be resolved. This then can affect the width in the scan axis which can be imaged using a line scan system, but these concerns can be addressed by using tight focusing of the excitation beam in the scan axis, and a high flux density.

According to various embodiments, the imaging system can be, for example, the imaging system shown in FIG. 1. The imaging system can comprise a light source such as a white light source, and a switching excitation filter, an emission filter and a beam splitter. A multi-camera/imaging system, such as a two camera system, can be considered for use with such an illumination system. In some embodiments, the system can comprise four cameras. A four camera system can comprise a white light illumination system. In such a system, a Rugate filter set can be utilized to enable four simultaneous bandpasses. Either a Rugate filter or a dichroic filter can be used to enable two excitation bandpasses. The excitation source can comprise a white light source, one or more lasers, or other possible illumination combinations. The system can comprise, for example, two standard dyes and two big dyes (with a larger Stokes shift), four standard dyes, a big dye set, two standard dyes and three big dyes, or other dye combinations.

In some embodiments, the system could comprise a dispersive element such as a grating prism or prism, with the dispersion orthogonal to the direction of the scan, to create a spectrum of light. The beads, single molecules or other targets can be placed on a fixed grid, and the spacing orthogonal to the scan direction can provide sufficient distance to accommodate the dispersion of the grating.

According to various embodiments, the system can be configured similarly to the existing imaging systems. Alternatively, a scanning system can be configured and utilized for this purpose, including a point scanner, a line scanner, and an image scanner (e.g. a TDI scanner as shown by way of example below in FIG. 2). In some embodiments, the system can comprise a point scanner. A point scanner can be configured in many ways, for example, the detector for a point scanner can comprise a single detector, used for a single channel of detection. A beam-splitter or a set of beam-splitters can be used permitting two or more channels of detection simultaneously. The excitation can have a single bandpass, or can have multiple bandpasses simultaneously or in serial.

In various embodiments, one can optimize the throughput of the system, for example, by optimizing the acquisition rate or the pixel readout rate (number of pixels per second). This can be accomplished using a detector, for example, a multi-tap CCD, a CMOS device, or other detector. The detector can be configured to operate in TDI mode. When the system is in TDI mode, an excitation source can be configured to provide excitation light beam that is the width of a bead, or wider than a bead. In some embodiments, the excitation source can be configured to provide excitation light beam that is half the width of the bead or less.

According to various embodiments, beads can be on the order of one micron in diameter. The detector can achieve an optical resolution of 500 nm, which is near the theoretical diffraction limit using a NA lens. When the system is configured with a detector that operates in TDI mode, the TDI device provides a mechanism that can allow the beam to be much wider than a pixel, as it has a number of pixels in the scanning direction. Additionally, the larger imaging area can allow imaging of the entire laser line, even if it is several microns in width. In this configuration, the system can illuminate and optically combining multiple beads in a scan axis. In some embodiments, if a pixel width in the scan axis corresponding to one micron is used, the optical resolution can be convolved with the pixel width, resulting in an effective width of 1.5 microns. Thus if one micron beads were close to each other, they could not be resolved. This then limits the width in the scan axis which can be imaged using a line scan system, further requiring tight focusing of the excitation in the scan axis, and requiring a high flux density. A TDI detection device can be configured to provide a mechanism by which to permit the beam to be much wider than a pixel, as it has a number of pixels in the scanning direction. Additionally, the larger imaging area can permit imaging of the entire excitation line in the scan axis, even if it is several microns in width, thus potentially illuminating and optically collecting from multiple beads in the scan axis simultaneously.

In various embodiments, the system can comprise a feedback system. The scanning speed of the stage can be synchronized with the clocking speed of the TDI camera or imaging apparatus using the feed back system. The system can comprise a linear encoder with resolution finer than the size of the beads or the pixel size in image space. In some embodiments, the pixel size of a detector is several microns wide. When a 20× system magnification is used, each pixel can correspond to about a third of a micron at the bead array. Thus, the resolution of the linear encoder can be significantly less than a third of a micron. The linear encoder can be modified to match changes in the size of beads, or to match the spacing of attachment points of single molecules or other areas of interest to be imaged.

In some embodiments, the feedback system can create information that can be outputted to inform the TDI detector or imaging system to clock in the horizontal direction (scan axis). With this information, the system can enable alignment between the detector image and the movement of the stage. To further optimize the system, each of the output taps of a TDI detection device can comprise an electron multiplying (EM) register. This approach can provide alignment between the different color images when using simultaneous imaging of multiple colors through the same detector.

In some embodiments, the substrate of the system can comprise one or more fiducials, for example, distinguishable markings on the substrate that can be used to help maintain the position maps of each bead or spot. Fiducials can be regularly spaced, for example, masked metal fiducials or random, such as bound particles that are reflective, fluorescent, or colored that have been scattered randomly on a slide. Fiducials can correct for unanticipated changes in position. For example, thermal expansion or unexpected motion of the slide relative to an optical rule might cause errors. Information about the fiducials can be with each bead or spot and can be stored in the system. This can dramatically reduce any subsequent data processing load. Further, a single image map can be stored, and portions of that map can be accessed at the same time that the same area is being scanned. The currently local area can then be the only area which is processed, minimizing the size of arrays associated with the image and map which are processed, for example, deconvolution of the system point spread function (PSF).

In some embodiments, chromatic aberration and differences in transmission across the detector can be addressed. The system can comprise multiple detectors, for example, a detector for each separate color of emission fluorescence. Each detector can comprise a focus adjustment, which can adjust each detector to overcome chromatic aberration in the objective. The detector can comprise correction factors to insure proper alignment between color channels. As mentioned previously, the system can comprise a beam shaper. Intensity variations due to various factors, including vignetting can be compensated for utilizing a beam shaper. The beam shaper can provide a variation in the intensity profile which can increase the flux in those areas at the target which appear as having less signal at the image. The beam shaper can provide uniform signal across the image.

In some embodiments, the system can be used in a single molecule detection system. One issue for a system that deals with single molecules is the turnover time of the fluorophores. In general, in order to get sufficient signal to noise ratio, a minimum observation time is desired to permit sufficient photons to be emitted. A higher excitation power might simply saturate the fluorophore, and would result in very few additional photons. Therefore, to fully utilize a scanning detector configured to operate in TDI mode, the detector can be kept it in use for a prolonged time period, to prevent saturation of the pixels. For example, if the scan distance is relatively short, then a majority of the time may be spent turning around at the ends of the scan, rather than actually scanning. There is a further issue that if it desirable to perform scans in quick succession, one to read the fluorophore, and one to confirm that it has been photocleaved, then the time between the scans may be equal at different points on the array.

According to various embodiments, multiple excitation wavelengths can be used to detect multiple sample components. According to various embodiments, the apparatus and method can be adapted for use by any suitable fluorescence detection system. For example, various embodiments of the apparatus and method can be used in a sequencing system with single or multiple samples, for example, in a nucleic acid sequence amplification reaction, in a sequencing detection system.

According to various embodiments, the system can comprise a scanning detector that scans in one direction, scanning a first row, then steps one scan width in the axis orthogonal to the scanned row, and scans back the other direction, scanning a second row. Alternatively, the system can comprise a scanning detector that uses a flyback scan, wherein the detector scans a row, then returns back to its original position, and then steps one scan width in the axis orthogonal to the scanned row, and repeats. If a photocleavage step is desired, two laser lines can be projected through the detector, one to perform the photocleavage, for example, at about 355 nm, and one to excite the dyes, for example, at about 488 nm. The system can also comprise three lasers, two excitation lasers, and one laser for photocleavage. Alternately it may be desirable to have one or more of the laser lines external to the objective. This reduces issues with fluorescence and scatter from the optical elements of the objective. The lasers can be configured to track with the objective so the excitation light stays on the same part of the image.

In various embodiments, when the system is used to detect single molecule sequencing, the spacing between the excitation lasers is generally not critical if the entire excitation beam is contained within the image area of the scanning detector. In some embodiments, the excitation beam can overfill that imaging area of the detector. In some embodiments, the excitation beam can under fill the imaging area of the detector. Where photocleavage is to be performed, the timing can be important, as the time between (and during) the photocleavage and the excitation can permit a first and or a second dNTP to incorporate, resulting in potential for a deletion error. Thus, in various embodiments, the width of the photocleavage laser line can be optimized to prevent raising the flux density to the point where photo-damage of the fluorophore polymerase or the dNTP might otherwise occur. In addition the system can be configured such that the space between the photocleavage laser line, the excitation laser line, and the width of the excitation laser line, can be controlled.

In various embodiments, a rotary stage may be used, avoiding stage stopping or direction reversal. This can be combined with an R stage. The wells or molecule locations can further cover the entire surface, or can be in tracks, which may occur as radial bands, or as a spiral. If radial bands are used, the bands can comprise a short gap in them, permitting the translation of the detector in the radial axis without wasting sample beads or molecules, or exposing part of the band to the excitation and or cleavage light more than once per scan In some embodiments, the system can be used to detect radial beads or a rectilinear array of beads. If radial bands are detected, the bands can comprise a gap in them to prevent wastage of sample beads or molecules. If a rectilinear array of beads is detected, the detector can scan one way as shown in the FIGS. 3-5.

In some embodiments, it may be desirable to either turn off the laser(s), or to shutter them while the detector returns to the other side, or performs a flyback. If multiple bands (corresponding to multiple scans) are used, either in a rectilinear scanner or a rotary scanner, the multiple bands can be separated so that the area illuminated orthogonal to the scan axis can be slightly larger than the image distance orthogonal to the scanner. This can insure that the entire imaged area is illuminated, without also illuminating a portion of the next band/scan. This spacing should take into account both the tolerance in aligning the image area and the illumination area, and any tolerance in the size of the image and or illumination area due to different levels of magnification resulting from different optical paths or variations from shaping the illumination beam.

As shown in FIGS. 3-5, the system can comprise a flow cell with flyback, or there can be multiple flow cells with flyback and translation between flow cells. The system can comprise multiple bands in a single flow cell, with flyback and translation between bands. Alternatively the orientation of the excitation and cleavage can be reversed, permitting scanning in alternate directions, removing the need for flyback. In one exemplary embodiment, the total area of the flow cells can be approximately the same size. In one embodiment it may be desirable if the UV and excitation light do not go through the objective, both to eliminate background and to permit total internal reflection fluorescence (TIRF) without using an immersion objective. In some embodiments, it can be preferable that the illumination areas are not Gaussian, but can, in some embodiments, be of a "top-hat" shape or of a shape that compensates for collection efficiency differences caused by vignetting. The size of the excitation illumination width can be close to the size of the detected imaging area; for example 128 pixel lines/3 lines/micron=about 43 microns. The size of the UV photocleavage illumination width can be the time needed for photocleavage divided by the time per pixel line/lines/micron; for example 25 msec/(1/50,000 lines/second)/3 lines/micron=417 microns. The size of the photocleavage area can be determined in part by a maximum flux density, in order to minimize photo damage.

In various embodiments, the system can be configured to in a system to detect synchronous single molecule sequencing (sSMS). The sSMS can use internally quenched dNTPs as substrates for an immobilized processive polymerase. It is noted that the dNTPs do not necessarily require total quenching and other labeled dNTP constructs may be used as substrates. In an exemplary application, an acceptor dye may be attached to each base through a photocleavable linker (PCL) and a dark quencher may be attached to the poly-phosphate terminus. Upon incorporation of a deoxyribonucleotide (dNTP) by the polymerase, the dark quencher containing polyphosphate may be cleaved and dissociated. Consequently, the dye on the base is then unquenched, and can be used to signal or detect the indication of an incorporation event. In various embodiments, when the newly incorporated base has been identified or the incorporation event registered, the dye can then be released by photocleavage or otherwise inactivated to allow for additional base incorporation events to occur. Exemplary systems configured to perform sSMS detection are exemplified in U.S. Patent Application Publication. Nos. US 2005/0244863 A1, to Mir, and US 2008/0003571 A1, to McKernan et al., and in International Publication No. WO 96/27025, to Rabini, all of which are incorporated herein by reference, in their entireties.

In some embodiments, the photocleavage and detection steps can be performed in a substantially synchronous manner to provide a convenient method by which to conduct sequencing of single molecules. In various embodiments, subsequent nucleotide incorporation is not expected until photocleavage of the fluorescent label for the base has occurred. Thus sSMS provides a valuable manner with which to separate and discriminate incorporation events from binding events.

In some embodiments, the time period for detection can be fixed, and the detection time period can be set large enough to provide sufficient signal to prevent deletion errors due to insufficient collection of photons, or due to base miscalls which result from having insufficient signal to detect a base, or insufficient signal to accurately determine which color, and thus which base was incorporated. At the same time the time period can also be set low enough to limit excessive illumination which can cause photoactivated degradation of the dyes, enzymes, or DNA.

An exemplary method for performing the above-described process includes the steps of:
(1) performing dNTP extension of the desired template(s) to incorporate a single labeled nucleotide whereby a quencher is released from each labeled nucleotide to thereby allow detection of the nucleotide(s);
(2) conducting an imaging operation to detect the newly incorporated nucleotide(s);
(3) performing a photocleavage operation wherein the dye associated with the newly incorporated nucleotide(s) is released or otherwise inactivated to permit detection of subsequent incorporation events; and
(4) Repeating steps (1) through (3) for subsequent base extensions.

In consideration of the stochastic properties of incorporation and photocleavage one may consider the incorporation rates of dNTPs by a selected polymerase. In general, a value may be ascribed to the turn over rate of the polymerase, which is often represented as an average value with a distribution generally around the average value. It will be appreciated that some polymerases have a faster turn over rate than others. The cycle time can be similar to the incorporation rate or longer if desired. Longer cycle times can allow most of the incorporations to occur for greater sequencing throughput but overall run time and device size will be increased.

According to various embodiments, the time it takes to incorporate a single labeled nucleotide (incorporation time) can include diffusion, binding, and/or incorporation, which can vary over a wide range of time. In various embodiments, incorporation time comprises an exponential decay. The distribution of incorporation time can follow an exponential decay. During the incorporation time, a decision can be made as to what period of time should lapse before imaging. In one aspect, the system can wait long enough to allow approximately 95% or more of the polymerase DNA complexes immobilized on a nanochip or substrate to have sufficient time to incorporate one base (either the polyermase or the DNA can be immoblized). This can be recognized as a tradeoff between system throughput and the size of the reaction area. The time between scans can depend on average incorporation time and the distribution width at a given certain percentage level. For example, if the average incorporation time is estimated to be approximately 200 ms (5/s), also called the time constant, then in 1000 ms, approximately 99% of the polymerases will be expected to have finished incorporation. For photocleavage, the measured time constant can be approximately 5 ms. Thus, in one example, if the incorporation bases were exposed to photocleavage (e.g. UV light cleavage) at same, approximately 99% of the dye molecules can be cleaved away in approximately 25 ms.

For photocleavage, the measured time constant may be approximately 5 ms for a particular flux level. Thus, in one example, if the incorporated bases were exposed to photocleavage (e.g. UV light cleavage) at the same flux level, approximately 99% of the dye molecules may be cleaved away in approximately 25 ms. Un-cleaved dyes can be detected during a second detection. The results can be use to calculate an insertion error.

According to some embodiments, the cycle time for a single modified base detection can be determined as follows: (average incorporation time)×5+(exposure time+readout time)+(average photocleavage time)×5=1.025+image time. Considering the overlap of the two distributions, a fraction of quickly incorporated modified bases can be photocleaved without being detected. By doing this, there can be photocleavage and incorporation during 1 photocleavage cycle. A larger ratio between the two time constants (incorporation/photocleavage) can result in a smaller error from this source. In asynchronous SMS (aSMS), a slower camera can result in a higher risk of missing a fast incorporation event. aSMS refers to real time SMS where incorporations can occur any time depending on the enzyme kinetics. If the incorporation rates, and/or the binding and incorporation times, between the four bases have different distributions, then there will likely be systematic error in sequencing for aSMS. The systematic error will be less for sSMS because the system can control the dNTP concentrations to normalize the incorporation rate for each base, and the variation in binding and incorporation times are not a significant part of the cycle time.

In considering stochastic properties of single molecule sequencing, which in some respects reflects the distribution of incorporation time and photocleavage time one can approximate the distribution as a simple exponential decay as shown in FIGS. 9 and 10. The average value can be used as one time constant where:

For incorporation: average incorporation rate is approximately 5 base/s; the time constant is approximately 0.2 s; and 5 times the constant is approximately 1 s (approximately 99% of features will have a dNTP incorporated).

For photocleavage: time constant is approximately 5 ms; 5 times the constant is approximately 25 ms (approximately 99% of dyes will be cleaved away, see FIGS. 9 and 10).

According to various embodiments, to avoid cleaving-incorporating-cleaving again all during the same photocleavage event, the two time constants can be significantly different (in this case the ratio is approximately 0.2/0.005=40). An exemplary process can comprise the following steps: trigger elongation, wait approximately 1 s for approximately 99% reaction completion, image approximately 1 s (preferentially for as many pixels as practical with a given camera or imaging apparatus), perform photocleavage for approximately 25 ms, and return to the original position to start image again.

An exemplary throughput calculation can comprise:
1 s×50,000 pixel/s=50,000 pixels,
Number of features in length=50,000/3=16,666,
Number of features in width=2048/3=682,
Total features=11.4 M,
1000 bases/reaction,
One reaction time=1×1000=1000 s,
Reaction number/day=86400/1000=86.4,
Throughput/day=number of features×reaction number/day×1000 bases/reaction, =985 GB/day.

In some embodiments, the flow cell, channel, or channels within the substrate can comprise a width of approximately 11.3 mm², with a pitch of 1 uM.

FIG. 11 shows an exemplary set of prisms 500 that can be used as modulating optics to modulate one or more excitation beams and/or one or more emission beams during a scanning operation according to various embodiments of the present teachings. In FIG. 11, set of prisms 500 is shown configured to modulate an excitation beam, for example, a laser beam. Set of prisms 500 can comprise a first prism 502 positioned adjacent and configured to move with an objective lens (not shown) of a detector (not shown), as the objective lens scans a substrate to detect emissions. Set of prisms 500 also comprises a second prism 504 that is configured to be fixed in position with respect to an excitation source (not shown). Set of prisms 500 also comprises a trombone prism 506. First prism 502 and second prism 504 are configured to operate in conjunction with trombone prism 506 such that the distance an excitation beam travels from its excitation source to any point on the substrate can be the same, thereby rendering the intensity of the excitation beam consistent regardless of what portion of the substrate is being scanned. According to various embodiments, such a system can prevent changes in the loss of excitation beam intensity at edge or corner locations of the substrate.

As shown in FIG. 11, set of prisms 500 can be configured on a translation stage such that first prism 502 can move with the objective of the detector, at a first rate of travel. Trombone prism 506 can be configured on the same translation stage or on a different translation stage but such that trombone prism 506 can move at a second rate of travel that differs from the first rate of travel. In the embodiment depicted, the first rate of travel is twice the second rate of travel such that, as the objective moves from a first edge of the substrate to an opposite edge of the substrate, first prism 502 and trombone prism 506 move at different rates. Over the same length of time, first prism 502 moves twice as many distance units, specifically, 200.000 distance units, as the number of distance units traveled by trombone prism 506, specifically, 100.000 distance units. Compare the positions of the prisms of set of prisms 500 in the first position identified in FIG. 11 with the positions of the prisms in the second position identified in FIG. 11. It is noted that numbers shown in FIG. 11 which contain decimal points are not reference numbers but instead are relative units of distance.

A set of prisms the same as, or similar to, that shown in FIG. 11 can be used for modulating emission beams according to various embodiments.

FIGS. 12A and 12B demonstrate representative excitation efficiency curves and fluorescence intensity curves, respectively, plotted versus wavelength for four different dye markers that can be used in detecting sequencing reactions according to various embodiments, namely, the dye markers 5-FAM, JOE, TAMRA, and ROX. These dye markers are exemplary of those that can be used in various embodiments where a plurality of dye markers are to be used.

In FIG. 12A, the x-axis corresponds to wavelengths, expressed in nanometers (nm), emitted by an excitation source. The y-axis corresponds to the percentage of excitation efficiency. As shown in FIG. 12A, 5-FAM has a maximum absorbance, corresponding to its peak percent excitation efficiency, at about 490 nm. When maximum absorbance of a dye marker occurs at a given wavelength, it indicates that the dye marker fluoresces at its peak fluorescence intensity when it is irradiated at that given wavelength. As further shown in FIG. 12A, JOE has a maximum absorbance at about 526 nm, TAMRA has a maximum absorbance at about 560 nm, and ROX has a maximum absorbance at about 588 nm. FIG. 12A also shows that, when a dye marker, such as 5-FAM, is irradiated at its maximum absorbance wavelength, other dye markers, such as, for example, JOE, TAMRA, and ROX, do exhibit some absorbance, although to a lesser extent than 5-FAM. Any excitation source, for example, a multiple laser excitation source, can be used to emit the wavelengths indicated on the x-axis.

According to various embodiments, fixed locations on a substrate, for example, on or in a substrate containing channels, can be scanned while being irradiated with multiple color irradiation sources, for example, multiple color lasers or multiple color LEDS. In some embodiments, one irradiation source can generate a first wavelength range of light that can be used as an excitation beam to excite detectable markers, while another irradiation source, used in conjunction with the first irradiation source, can generate a second wavelength range of light that can be, but is not necessarily, different from the first wavelength range. The second wavelength range can be designed to photocleave protective groups from protected polynucleotides, for example, so that a subsequent nucleotide incorporation step can occur.

According to various embodiments, an irradiation source can be conditioned to provide only a narrow wavelength range of light. A bandpass filter can be used to substantially block all of the unwanted irradiation from the irradiation source. As used herein, "irradiation source" can include one or more sources of irradiation. An example of the results, in the form of graphs demonstrating the effects of a conditioned irradiation source in combination with a bandpass filter, are illustrated in FIGS. 13A through 13D.

According to various embodiments and as depicted in FIGS. 13A through 13D, locations on a substrate can be irradiated by two irradiation sources simultaneously, although any number of irradiation sources can be used simultaneously according to various embodiments. Associated optics can be altered according to the number of irradiation sources used.

According to various embodiments, a conditioning filter can be used for each irradiation source or set of irradiation sources. The conditioning filter can substantially block predetermined ranges of wavelengths of light emitted by the set of irradiation sources, as previously described. Each predetermined range that irradiates can correspond to a respective excitation wavelength, as demonstrated, for example, in FIG. 13A, or one can correspond to an excitation wavelength range while another corresponds to a photocleavage wavelength range. FIG. 13A shows a graph of relative irradiation intensity for each of two irradiation sources of a set of irradiation sources, versus wavelength expressed in nanometers. The graph of FIG. 13A depicts the two irradiation sources as generating beams in the violet and orange portions of the spectrum, respectively. It is to be understood that various embodiments are not limited to the above types of irradiation sources, but encompasses any number of irradiation sources emitting light in any range of frequencies according to application needs. As depicted in FIG. 13B, each predetermined range of wavelengths that passes through the conditioning filter corresponds to a subset of the wavelengths emitted by each respective irradiation source depicted in the graph of FIG. 13A. The wavelengths that pass through the conditioning filter can be capable of exciting the markers responsive to each respective irradiation source.

FIG. 13B is a graph of percent transmission of light through the conditioning filter versus wavelength. As shown in FIG. 13B, the conditioning filter can substantially block all irradiation light except for wavelengths around the respective excitation range maximum. For example, the conditioned light ranges can correspond to a wavelength range of from about 450 nm to about 490 nm, and to a second wavelength range of from about 580 nm to about 605 nm, corresponding to the first and second irradiation sources, respectively. The conditioning filter, and the predetermined ranges capable of passing there through, can be functions of the irradiation set being used.

According to various embodiments, the conditioning filter can include a single conditioning filter, or a series of conditioning filters, capable of filtering the light from the set of irradiation sources, and as described in more detail above. The conditioned light can be focused onto a substrate to be scanned, as previously described above.

FIG. 13C depicts percent light transmission plotted versus wavelength. According to various embodiments, the bandpass filter can allow light corresponding to the "blue," "green," "yellow," "red," and "orange" markers to pass through. The regions or zones corresponding to the irradiation light of the irradiation sources can be blocked. According to various embodiments, the bandpass filter can include a single bandpass filter, a series of bandpass filters capable of filtering the light from the irradiation sources, a multi-notch filter, or a Rugate filter.

FIG. 13D depicts a plot of relative emission intensity versus wavelength, expressed in nm, for the filtered light. FIG. 13D, in effect, provides a breakdown, by wavelength, of the light transmitted through the exemplary bandpass filter. As shown in FIG. 13D, the markers excited by an excitation source of the irradiation sources used in the example of FIGS. 13A through 13D emit light in the "blue," "green," "yellow," "red," and "orange" ranges of wavelengths. Before focusing the light signals thus filtered onto the detector array of a CCD, a dispersion element can be used, such as a grating. TDI can be performed during data collection with the above-described system embodiments.

FIGS. 14-21 depict various substrates, substrate locations to be imaged, image arrays for use therewith, and excitation beam shapes that can be used in a time-delay integration mode according to various embodiments of the present teachings. FIG. 14 is an image of a substrate 700 comprising a plurality of locations 702 arranged in an orderly array 704. Substrate 700 has been scanned according to various embodiments of the present teachings. The image represents a square portion of substrate 700.

FIG. 15 is an image of a substrate 710 comprising a plurality of locations 712 arranged in an non-orderly array 714. Substrate 710 has been scanned according to various embodiments of the present teachings. The image represents a square portion of substrate 710.

FIG. 16 is a broken view of a substrate 720 comprising a plurality of locations 722 arranged in an orderly array 724. The substrate is to be imaged according to various embodiments of the present teachings. The laser excitation beam used to excite markers at locations 726 is in the form of a line 728 that has a width that is only about half of the width of each location 726 along the line.

FIG. 17 is a top view of a linear image array 730 aligned above the line of locations 726 shown in FIG. 16, which has been irradiated with the excitation beam line 728 shown in FIG. 16. Pixels 732 of linear image array 730 are shown centered with respect to the line of locations 726. Plural pixels 732 are shown above each location 726 in the line. The narrow width of laser line 728 prevents blurring during scanning, but can be difficult to form as it may lead to diffraction limited in the scan axis.

FIG. 18 is a broken view of a substrate 740 comprising a plurality of locations 742 arranged in an orderly array 744. Substrate 740 is to be imaged according to various embodiments of the present teachings. A laser excitation beam 746 is used to excite markers at a line of locations 748. Laser excitation beam 746 is in the form of a line that has a width that exceeds the width of each location 748 along the line of locations.

FIG. 19 is a top view of a linear image array 750 aligned above the line of locations 748 shown in FIG. 18. Line of locations 748 has been irradiated with excitation beam 746 shown in FIG. 18. Pixels 752 of linear image array 750 are shown centered with respect to the line of locations 748. Plural pixels 752 are shown above each location 748 in the line of locations. Each pixel 752 of linear image array 750 has a width that is less than the width of the respective location 748 being imaged. The narrow width of pixels 752 prevents blurring during scanning, but may result in loss of photons emitted, as laser line 746 may illuminate areas which are not imaged.

FIG. 20 is a broken view of a substrate 760 comprising a plurality of locations 762 arranged in an orderly array 764, wherein substrate 760 is to be imaged according to various embodiments of the present teachings. As shown in FIG. 20, a laser excitation beam 766 has been shaped into the form of an area beam that irradiates an area 768 having a width equal to the width of five lines of locations. As shown area 768 can encompass many locations that can be simultaneously irradiated with excitation beam 766.

FIG. 21 is a top view of a two-dimensional image array 770 aligned above the five-line area of locations 768 shown in FIG. 20. Area of locations 768 (FIG. 20) has been irradiated with area excitation beam 766 shown in FIG. 20. Pixels 772 of two-dimensional image array 770 are shown above the area of locations 768, and as can be seen, plural pixels 772 are shown above each location 762 in area of locations 768. Each pixel 772 of two-dimensional image array 770 has a width that is less than the width of the respective location 762 being imaged. Two-dimensional image array 770 can be operated in a time-delay integration mode. Two-dimensional image array 770 has neither of the potential limitations exhibited by the linear scanner previously described. It can image the entire laser line, and the laser line can be relatively easy to generate. Further, perfect alignment between the laser line and the image array is not necessary.

Various alternatives to the embodiments of the teachings described herein are also within the scope of the present teachings. The teachings are not limited to the specific embodiments described, but encompass equivalent features and methods as would be known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. A polynucleotide sequencing system, comprising:
a flow cell having at least one channel, a plurality of polynucleotides disposed in the at least one channel, at least a portion of the plurality of polynucleotides comprising a detectable label;
a first irradiation source configured to generate a first excitation beam which irradiates a first group of polynucleotides of the plurality of polynucleotides thereby exciting at least one detectable label of at least one polynucleotide of the first group of polynucleotides such that the at least one detectable label of the at least one polynucleotide of the first group of polynucleotides emits an emission signal;
a second irradiation source configured to generate a second excitation beam which irradiates a second group of polynucleotides of the plurality of polynucleotides thereby exciting at least one detectable label of at least one polynucleotide of the second group of polynucleotides such that the at least one detectable label of the at least one polynucleotide of the second group of polynucleotides emits an emission signal, the second group of polynucleotides being different from the first group of polynucleotides, the first and second excitation beams simultaneously irradiating the first and second groups of polynucleotides, respectively, wherein the first excitation beam does not substantially overlap the second excitation beam;
a detection system having at least a first detector configured to detect the emission signal from the at least one detectable label of the at least one polynucleotide of the first group of polynucleotides and having at least a second detector configured to detect the emission signal from the at least one detectable label of the at least one polynucleotide of the second group of polynucleotides, the first and second detectors configured to detect distinct wavelengths or wavelength ranges relative to one another corresponding to distinct nucleotides; and
a computer in operative communication with the detection system and configured to collect and process the detectable emissions from the first and second groups of polynucleotides.

2. The system of claim 1, wherein the first irradiation source comprises at least one laser source.

3. The system of claim 1, wherein at least one detector of the detection system comprises a charge-coupled device.

4. The system of claim 1, wherein the detection system comprises a point detector.

5. The system of claim 1, wherein at least one detector of the detection system comprises a time-delay integration image detector.

6. The system of claim 1, wherein the first group of polynucleotides partially overlaps the second group of polynucleotides.

7. The system of claim 1, wherein the first group of polynucleotides excludes the second group of polynucleotides.

8. The system of claim 1, wherein the plurality of polynucleotides and the first and second excitation beams are stationary relative to one another as the detection system detects emissions.

9. The system of claim 1, wherein the plurality of polynucleotides and the first and second excitation beams are moving relative to one another as the detection system detects emissions.

10. The system of claim 1, wherein the emission signal from the at least one detectable label of the at least one polynucleotide of the first group of polynucleotides is indicative of a nature of the at least one polynucleotide of the first group of polynucleotides, and the emission signal from the at least one detectable label of the at least one polynucleotide of the second group of polynucleotides is indicative of a nature of the at least one polynucleotide of the second group of polynucleotides.

11. The system of claim 1, wherein the emission signal from the at least one detectable label of the at least one polynucleotide of the first group of polynucleotides is indicative of a presence of a nucleotide of the at least one polynucleotide.

12. The system of claim 1, wherein the emission signal from the at least one detectable label of the at least one polynucleotide of the first group of polynucleotides is indicative of an identity of a nucleotide of the at least one polynucleotide.

13. The system of claim 1, wherein each detectable label is one of at least 4 distinct, fluorescent labels, each of the 4 distinct, fluorescent labels being indicative of a distinct result of a sequencing reaction.

14. The system of claim 13, wherein each of the 4 distinct, fluorescent labels are each indicative of the presence or nature of a distinct nucleotide.

15. A system for detecting emissions, comprising:
a flow cell comprising one or more channels, a plurality of polynucleotides in at least one of the channels;
a first irradiation source configured to generate a first radiation beam which irradiates a first group of polynucleotides of the plurality of polynucleotides, at least one polynucleotide of the first group of polynucleotides configured to emit a detectable emission in response to the first radiation beam;

a second irradiation source configured to generate a second radiation beam which irradiates a second group of polynucleotides of the plurality of polynucleotides, at least one polynucleotide of the second group of polynucleotides configured to emit a detectable emission in response to the second radiation beam, the second group of polynucleotides being different from the first group of polynucleotides, the first and second radiation beams simultaneously irradiating the first and second groups of polynucleotides, respectively, wherein the first radiation beam does not substantially overlap the second radiation beam;

a detection system having at least four time-delay integration detectors, the system configured to detect at least the detectable emission produced by the at least one polynucleotide of the first group of polynucleotides and the detectable emission produced by the at least one polynucleotide of the second group of polynucleotides, the system configured such that at least one of the flow cell, the first group of polynucleotides, the second group of polynucleotides, and the plurality of polynucleotides move relative to the at least four time-delay integration detectors during detection of the emissions by the detection system, each of the at least four time-delay integration detectors configured to detect a distinct wavelength or wavelength range relative to the other time-delay integration detectors, the distinct wavelengths or wavelength ranges corresponding to distinct nucleotides; and a computer in operative communication with the detection system and configured to collect and process the detectable emissions from the first and second groups of polynucleotides.

16. The system of claim 15, wherein a portion of the plurality of polynucleotides are labeled with a fluorescent label or fluorescent marker configured to emit an emission of an emission wavelength or wavelength range in response to being irradiated by an excitation wavelength or wavelength range.

17. The system of claim 16, wherein the first radiation beam includes a first excitation wavelength or wavelength range, and the second radiation beam includes a second excitation wavelength or wavelength range, the first excitation wavelength or wavelength range being different from the second excitation wavelength or wavelength range.

18. The system of claim 15, wherein the one or more channels comprises from two to 10 channels, and the detection system is configured to detect emissions from polynucleotides within at least two channels sequentially.

19. The system of claim 1, wherein the detection system comprises 4 detectors, each detector being a camera configured to detect an emission signal of a distinct wavelength or wavelength range, each wavelength or wavelength range corresponding to a distinct nucleotide.

20. The system of claim 1, further comprising a stage configured to support the flow cell, the stage further configured to move the flowcell relative to the first and second excitation beams.

21. The system of claim 1, wherein the polynucleotides are fixed relative to the channel.

22. The system of claim 21, wherein the at least one channel is formed at least in part between a top flow cell wall and a bottom flow cell substrate, at least a portion of the plurality of polynucleotides being disposed on an underside of the top flow cell wall, a portion of the polynucleotides disposed on the underside of the top flow cell wall comprising a detectable label.

23. The system of claim 21, wherein the system is configured to move the flow cell relative to the detection system such that the detection system detects emissions in a first direction along the flow cell, the system further configured to move the flow cell a distance in an axis orthogonal to a length of the at least one channel, and further configured to subsequently move the flow cell relative to the detection system such that the detection system detects emissions in a second direction along the flow cell.

24. The system of claim 1, further comprising more than one flow cell.

25. The system of claim 1, wherein the first excitation beam includes radiation of a first wavelength or wavelength range, and the second excitation beam includes radiation of a second wavelength or wavelength range, the first wavelength or wavelength range being different from the second wavelength or wavelength range.

26. The system of claim 1, further comprising modulating optics disposed between at least one of the first and second irradiation sources and the flow cell.

27. The system of claim 15, wherein the plurality of polynucleotides are fixed relative to the channel.

28. The system of claim 23, wherein the first direction is the same as the second direction.

29. The system of claim 23, wherein the first direction is opposite of the second direction.

30. The system of claim 1, wherein at least one detector of the detection system comprises a complimentary metal-oxide-semiconductor (CMOS) device.

31. The system of claim 15, wherein at least one detector of the detection system comprises a complimentary metal-oxide-semiconductor (CMOS) device.

* * * * *